US011179260B2

(12) United States Patent
Best et al.

(10) Patent No.: US 11,179,260 B2
(45) Date of Patent: Nov. 23, 2021

(54) KNEE BRACE DEVICES, SYSTEMS AND METHODS

(71) Applicant: Shock Doctor, Inc., Fountain Valley, CA (US)

(72) Inventors: William Best, Huntington Beach, CA (US); Thierry Petelle, Montreal (CA); Bastien Jourde, Montreal (CA)

(73) Assignee: Shock Doctor, Inc., Fountain Valley, CA (US)

( * ) Notice: Subject to any disclaimer, the term of this patent is extended or adjusted under 35 U.S.C. 154(b) by 126 days.

(21) Appl. No.: 16/205,740

(22) Filed: Nov. 30, 2018

(65) Prior Publication Data

US 2019/0091055 A1 Mar. 28, 2019

Related U.S. Application Data

(63) Continuation of application No. PCT/US2016/035841, filed on Jun. 3, 2016.

(51) Int. Cl.
*A61F 5/05* (2006.01)
*A61F 5/01* (2006.01)

(52) U.S. Cl.
CPC .......... *A61F 5/0123* (2013.01); *A61F 5/0109* (2013.01); *A61F 2005/0134* (2013.01);
(Continued)

(58) Field of Classification Search
CPC .............. A61F 5/0123; A61F 5/0109; A61F 2005/0141; A61F 5/0179; A61F 5/0134;
(Continued)

(56) References Cited

U.S. PATENT DOCUMENTS 4,908,037 A * 3/1990 Ross ................ A61F 2/80
2/22
5,277,697 A * 1/1994 France .............. A61F 5/0125
602/16
(Continued)

FOREIGN PATENT DOCUMENTS

DE 3210838 A1 10/1983
WO 2014/191895 A1 12/2014

OTHER PUBLICATIONS

International Preliminary Report on Patentability received for PCT Patent Application No. PCT/US2016/035841, dated Dec. 13, 2018, 11 pages.
(Continued)

*Primary Examiner* — Camtu T Nguyen
(74) *Attorney, Agent, or Firm* — Faegre Drinker Biddle & Reath LLP

(57) ABSTRACT

A knee brace comprising a frame assembly comprising an outer frame portion and an inner frame portion. The outer frame portion has a first outer transverse member, a second outer transverse member, and an outer side member configured to extend along a length of a first side of a user's leg when worn by the user, the outer side member extending between the first outer transverse member and the second outer transverse member. The inner frame portion has a first inner transverse member, a second inner transverse member, and an inner side member opposite the outer side member and is configured to extend along a length of a second side of a user's leg when worn by the user, the second side member extending between the first inner transverse member and the second inner transverse member. The outer frame portion and inner frame portion define a top portion of the frame assembly and a bottom portion of the frame assembly, the top and bottom portions configured to be pivotable relative to each other. The frame assembly addi-
(Continued)

tionally comprises a flex member connecting the inner frame portion and the outer frame portion in at least one of the top and bottom portions of the frame assembly. In embodiments, a securement system may be included to form a knee brace assembly or system.

10 Claims, 25 Drawing Sheets

(52) U.S. Cl.
CPC .............. *A61F 2005/0141* (2013.01); *A61F 2005/0176* (2013.01)

(58) Field of Classification Search
CPC ...... A61F 2002/7818; A61F 2002/7837; A61F 2002/735; A61F 2/7812
See application file for complete search history.

(56) References Cited

U.S. PATENT DOCUMENTS

| | | | | |
|---|---|---|---|---|
| 5,334,135 | A * | 8/1994 | Grim | A61F 5/0102 2/22 |
| 5,497,513 | A * | 3/1996 | Arabeyre | A61F 13/08 2/16 |
| 6,059,834 | A * | 5/2000 | Springs | A61F 2/7812 602/63 |
| 8,157,756 | B2 | 4/2012 | Schimek et al. | |
| 9,744,063 | B2 * | 8/2017 | Huffa | A61F 5/0109 |
| 2008/0082035 | A1 * | 4/2008 | Evans | D04B 21/16 602/60 |
| 2012/0089064 | A1 | 4/2012 | Chang | |
| 2012/0233736 | A1 * | 9/2012 | Tepper | A41D 13/0153 2/24 |
| 2014/0194801 | A1 * | 7/2014 | Thorsteinsdottir | A61F 5/0109 602/26 |
| 2016/0324675 | A1 * | 11/2016 | Gomez | A61F 5/30 |
| 2018/0042754 | A1 * | 2/2018 | Ingimundarson | D04B 1/22 |
| 2019/0328566 | A1 * | 10/2019 | Millet | A61F 5/0109 |

OTHER PUBLICATIONS

International Search Report and Written Opinion received for PCT Patent Application No. PCT/US2016/035841, dated May 4, 2017, 16 pages.

* cited by examiner

KNEE BRACE DEVICES, SYSTEMS AND METHODS

CROSS-REFERENCE TO RELATED APPLICATION

This application is a continuation of International Application No. PCT/US2016/035841, with an international filing date of Jun. 3, 2016, which is incorporated by reference herein in its entirety.

TECHNICAL FIELD

The instant disclosure relates to devices and methods for supporting a limb or limbs of a user when worn. More specifically, the instant disclosure relates to devices, systems, and methods for supporting a knee of a user when worn.

BACKGROUND

Devices for supporting or stabilizing the limb or limbs of a wearer may be worn by a user for everyday use and/or for use when engaging in physical activity. Injuries to a limb or limbs are common and may affect a user's physical ability and/or athletic performance. For certain users it may be beneficial to use an artificial structure to support a limb that has been weakened or injured. Certain rigid structures may be worn through the day and/or when engaging in sports to provide structural support, or prevent further injury. Often a physician or healthcare worker may apply a custom fitted support or structure to the outside of user's limb to provide weight bearing support to the user's limb.

Certain support structures for the leg or knee of a user, such as straps or braces, are available and may provide certain advantages such as agility, comfort, or weight bearing capabilities. However, certain options may be unsuitable because of particular characteristics. For example, sleeves that are currently available may be flexible or comfortable, but may not provide adequate support. In other instances, a custom fitted device may be costly and/or require extensive customization for a user. Additionally, certain devices that provide structural support may be uncomfortable, or unsuited for use in certain sports that require a particular level of agility or movement by the user's limbs. There is thus a need for a device or method for supporting a limb or limbs of a user that provides suitable weight bearing capability yet is flexible and comfortable enough to be used during sports and is also cost effective and accessible.

SUMMARY

Disclosed herein, in Example 1, is a knee brace comprising a frame assembly. The frame assembly comprises an outer frame portion and an inner frame portion. The outer frame portion has a first outer transverse member, a second outer transverse member, and an outer side member configured to extend along a length of a first side of a user's leg when worn by the user, the outer side member extending between the first outer transverse member and the second outer transverse member. The inner frame portion has a first inner transverse member, a second inner transverse member, and an inner side member opposite the outer side member and is configured to extend along a length of a second side of a user's leg when worn by the user, the second side member extending between the first inner transverse member and the second inner transverse member. The outer frame portion and inner frame portion define a top portion of the frame assembly and a bottom portion of the frame assembly, the top and bottom portions configured to be pivotable relative to each other. The frame assembly additionally comprises a flex member connecting the inner frame portion and the outer frame portion in at least one of the top and bottom portions of the frame assembly.

In Example 2, the knee brace of Example 1, further comprising a first articulation element and a second articulation element pivotably coupling the top and bottom portions of the frame assembly to each other.

In Example 3, knee brace of Example 2, wherein the first articulation element forms a part of the outer side member, and the second articulation element forms a part of the inner side member.

In Example 4, the knee brace of any of Examples 2-3, wherein the first and second articulation elements each comprises a first hinge and a second hinge configured to pivotably join the top and bottom portions to each other.

In Example 5, the knee brace of any of Examples 1-4, wherein the first outer transverse member and first inner transverse member are shaped to curve from a lateral side of a user's thigh across the front of the user's thigh to a medial side of the user's thigh, and the second outer transverse member and second inner transverse member are shaped to curve from a lateral side of a user's shin across a front of the user's shin to a medial side of the user's shin.

In Example 6, the knee brace of any of Examples 1-5, wherein the outer frame portion and inner frame portion define an opening configured to receive a knee of a user when worn.

In Example 7, the knee brace of any of Examples 1-6, wherein the flex member comprises a resilient structure configured to allow the outer frame portion to flex in relation to the inner frame portion.

In Example 8, the knee brace of any of Examples 1-7, further comprising a cushioning layer over molded around the outer frame portion.

Disclosed herein in Example 9 is a knee brace assembly, comprising a frame assembly and a securement system. The frame assembly includes a top portion and a bottom portion pivotably coupled to the top portion. The top portion includes a top outer frame section, a top inner frame section, and a top flex member positioned between and attaching the top outer frame section and the top inner frame section. The top outer frame section includes a top outer transverse member oriented to extend generally across at least a part of a thigh of a user when worn, and a top outer side member extending from the top outer transverse member and is oriented to extend generally along a first length of a first side of the thigh of the user when worn. The top inner frame section includes a top inner transverse member oriented to extend generally across at least a part of the thigh of the user when worn, and a top inner side member extending from the top inner transverse member and oriented to extend generally along a first length of a second side of the thigh of the user opposite the first side of the thigh of the user. The bottom portion includes a bottom outer frame section, a bottom inner frame section, and a bottom flex member positioned between and attaching the bottom outer frame section and the bottom inner frame section. The bottom outer frame section includes a bottom outer transverse member oriented to extend generally across at least a part of a shin of a user when worn, and a bottom outer side member extends from the bottom outer transverse member and is oriented to extend generally along a second length of the first side of the shin of the user when worn. The bottom inner frame section includes a bottom inner transverse member oriented to extend generally across at least a part of the shin of the user when worn, and a bottom inner side member extending from the bottom inner transverse member and oriented to extend generally along a second length of the second side of the shin of the user when worn. The securement system is configured to secure the brace assembly against the leg of a user.

In Example 10, the knee brace assembly of Example 9, wherein the securement system includes a plurality of straps configured to secure the frame assembly to a leg of the user.

In Example 11, the knee brace assembly of either of Examples 9 or 10, further comprising a first articulation element pivotably coupling the top outer side member to the bottom outer side member, and a second articulation element pivotably coupling the top inner side member to the bottom inner side member.

In Example 12, the knee brace assembly of Example 11, wherein the top outer frame section and bottom outer frame section are connected by the first articulation element to form a substantially C-shaped outer frame portion.

In Example 13, the knee brace assembly of either of Examples 11 or 12, wherein the top inner frame section and the bottom inner frame section are connected by the second articulation element to form a substantially C-shaped inner frame portion.

Disclosed herein, in Example 14, is a knee brace system, comprising a knee brace and a sleeve system. The knee brace includes a frame assembly having a top portion and a bottom portion. The top portion includes a top outer edge and a top inner edge, and the bottom portion includes a bottom outer edge and a bottom inner edge, wherein the top portion is pivotably coupled to the bottom portion. The sleeve system includes a tubular member having a first end defining a first opening, a second end defining a second opening, a length between the first and second ends, an inner surface, and an outer surface. The sleeve system tubular member is configured to receive a user's leg and the frame assembly is configured to be positioned over a portion of the tubular member when worn, whereby the frame assembly can be secured to the user's leg by positioning the first end of the tubular member about and around a part of the top portion of the frame assembly and positioning the second end of the tubular member about and around a part of the bottom portion of the frame assembly.

In Example 15, the knee brace system of Example 14, wherein the top portion of the frame assembly has an inner surface shaped to curve across a user's thigh, and wherein the bottom portion of the frame assembly has an inner surface shaped to curve across a user's shin when worn by a user.

In Example 16, the knee brace system of either of Examples 14 or 15, wherein frame assembly includes a first articulation element configured to be located on a lateral side of a user's knee and a second articulation element configured to be located on a medial side of a user's knee when worn by a user.

In Example 17, the knee brace system of any of Examples 14-16, further comprising a cushioning layer over molded around the top outer edge and bottom outer edge.

In Example 18, the knee brace system of any of Examples 14-17, wherein the frame assembly has an opening configured to receive a knee of the user when worn.

In Example 19, the knee brace system of any of Examples 14-18, wherein the tubular member further comprises a first cuff adjacent the first opening and configured to be folded over the top outer edge of the frame assembly when the frame assembly is positioned over the tubular member in use, and a second cuff adjacent the second opening and configured to be folded over the bottom outer edge of the frame assembly when the frame assembly is positioned over the tubular member in use.

In Example 20, the knee brace system of any of Examples 14-19, wherein the tubular member further comprises a pad configured to be located adjacent a user's knee and at least partially within or adjacent to the opening in the frame assembly when worn.

Disclosed herein, in Example 21, is a method of forming a frame assembly for a knee brace, the method comprising forming a first frame portion, forming a second frame portion, and attaching a first articulation element and a second articulation element to the first and second frame portions such that the first and second frame portions can pivot relative to one another. Forming the first frame portion includes providing a first outer frame member and a first inner frame member. The first outer frame member has a first outer transverse section, a first outer side section, an inner edge and an outer edge, and the first inner frame member has a first inner transverse section, a first inner side section, an outer edge and an inner edge. A first flex member is then over molding at least partially between the outer edge of the first inner frame member and the inner edge of the first outer frame member. Forming the second frame portion includes providing a second outer frame member and a second inner frame member. The second outer frame member has a second outer transverse section, a second outer side section, an inner edge and an outer edge, and the second inner frame member has a second inner transverse section, a second inner side section, an outer edge and an inner edge. A second flex member is then over molded at least partially between the outer edge of the second inner frame member and the inner edge of the second outer frame member.

In Example 22, the method of Example 21, wherein the first frame portion has an inner surface shaped to curve around a user's thigh when worn by a user, and wherein the second frame portion has an inner surface shaped to curve around a user's shin when worn by the user.

In Example 23, the method of any of Examples 21-22, wherein attaching the first articulation element to the first and second frame portions includes attaching the first articulation element to the first outer side section and to the second outer side section, and further wherein attaching the second articulation element to the first and second frame portions includes attaching the second articulation element to the first inner side section and the second inner side section.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
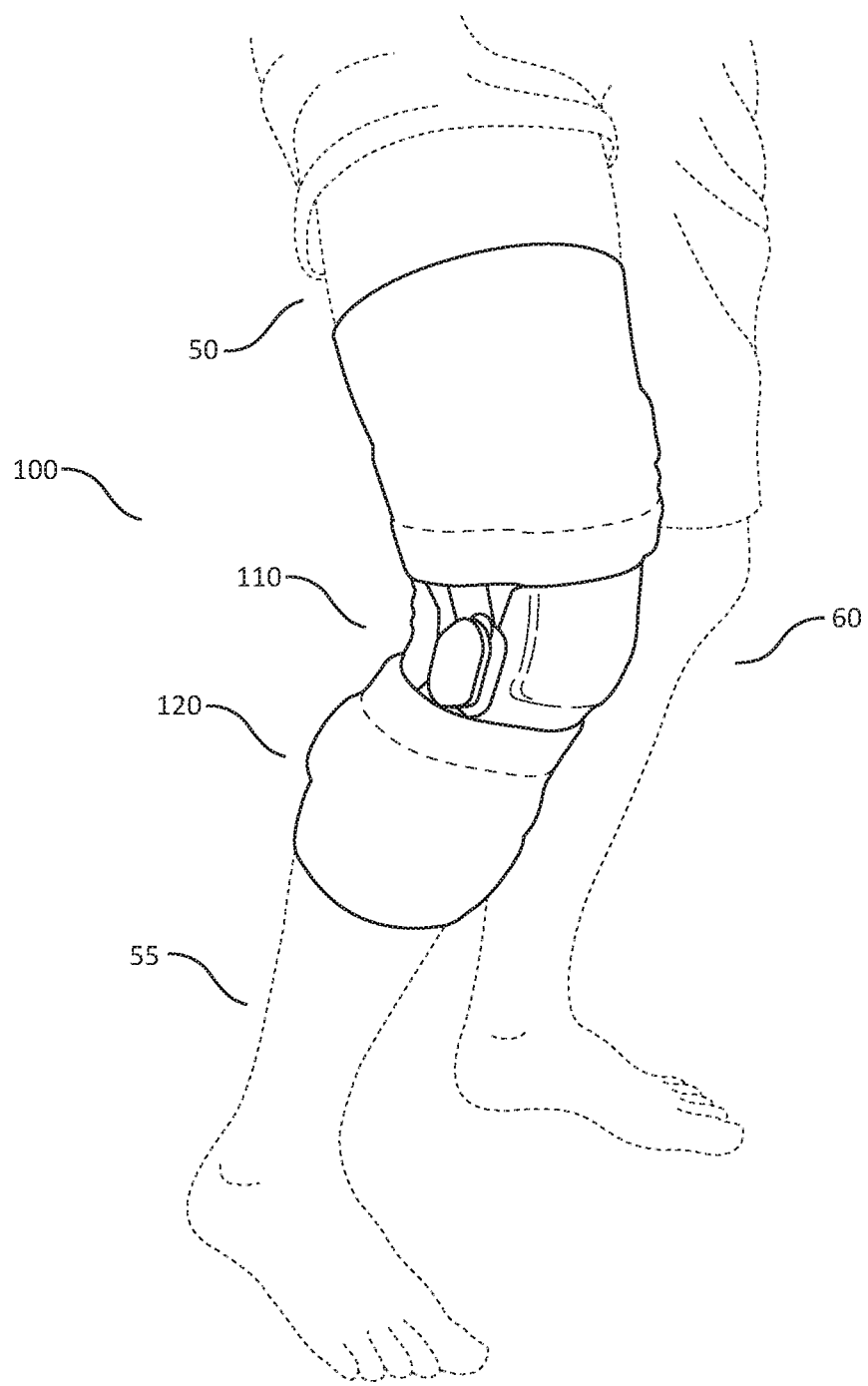
FIG. 1 is a perspective view of an embodiment of a knee brace system.

FIG. 1 is an overall schematic of a knee brace system 100, including a knee brace assembly 110, and a sleeve assembly 120. As shown in FIG. 1, the knee brace system 100 may be configured to be worn by a user to support a thigh 50 of a user, a shin 55 of a user, and/or a knee 60 of a user when worn. The knee brace system 100 may include rigid or semi-rigid support structures that are integrated to form an overall assembly for supporting the leg and/or knee of a wearer. The knee brace system 100 may have a structure configured to be located around a user's knee 60 or knee joint with an articulation that may hinge with a user's thigh 50, shin 55, and/or knee 60 and provide support, and includes flex zones for a semi-rigid fit. In some embodiments, an over-molded flexible or resilient connection between the components of the knee brace system 100 allows for an active self-adaptive flex-fit of the brace to be possible when a user's leg is flexing.

Knee Brace Assembly

Figure 2:
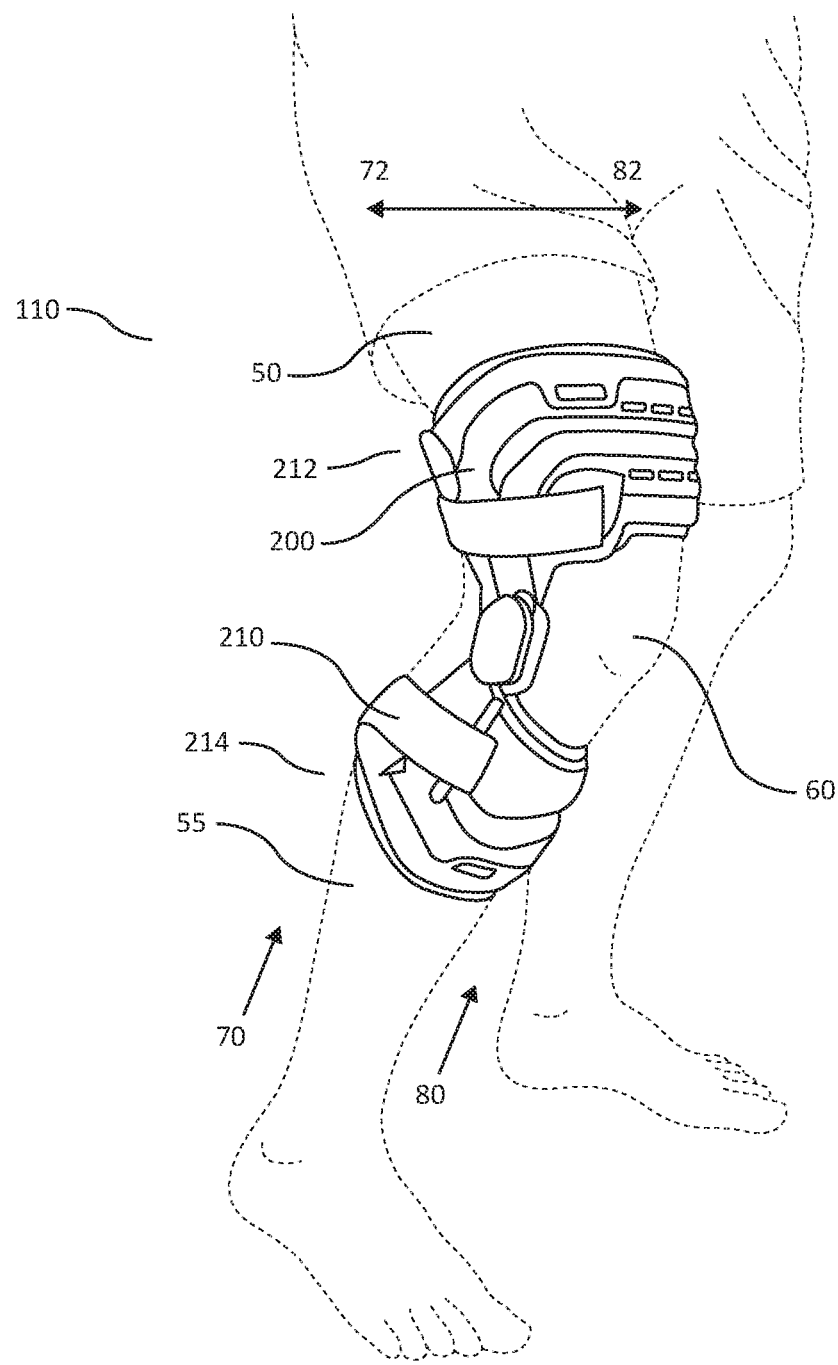
FIG. 2 is a perspective view of an embodiment of a knee brace assembly.

FIG. 2 is an overall schematic of a knee brace assembly 110. As shown in FIG. 2, in some embodiments, the knee brace assembly 110 includes a frame assembly 200 and a strap arrangement 210. As shown in FIG. 2, the knee brace assembly 110 is configured to be worn by a user with a first portion 212 located generally on the thigh 50 of a user, and a second portion 214 located generally on a shin 55 of a user. The strap arrangement 210 may be used to retain the frame assembly 200 against the thigh 50 and/or shin 55 of the user. The strap arrangement 210 may be used to retain the frame assembly 200 in position relative to the knee 60 of the user when worn. The knee brace assembly 110 may be formed with a first side 72 and a second side 82. For example, the knee brace assembly 110 may be formed to have a suitable fit with a lateral side 70 of a user's leg and/or knee, and a suitable fit with a medial side 80 of a user's leg and/or knee when worn by the user.

As shown in FIG. 2, the knee brace assembly 110 may be configured to be worn on a right leg of a user. In some embodiments, the knee brace assembly 110 may be configured to be worn on a left leg of a user. It is envisioned that a suitably shaped knee brace assembly 110 may be formed to be worn on either of a right leg of a user or a left leg of a user. That is, the knee brace assembly 110 may be configured to be interchangeable between a right leg or a left leg of a user. In some embodiments, a knee brace assembly 110 may be formed to be worn on only a right leg, or only on a left leg of a user. For example, the knee brace assembly 110 may be shaped to be used only on either a right leg or a left leg of a user. For example, a knee brace assembly 110 may be formed having a first side 72 made to be located on the lateral side 70 of a user's leg and/or knee, and a second side 82 made to be located on the medial side 80 of a user's leg and/or knee when worn.

As used herein, "medial" refers to a location toward the middle, midline, or median plane of a user's body. As used herein, "lateral" refers to a location toward the side or outside of a user's body. That is the medial side of a user's leg is the side that faces generally inward toward the center of the body, i.e. toward the opposing leg. The lateral side of a user's leg is the side that faces generally outward from the user's body, i.e. away from the opposing leg and away from the medial side of the same leg. Thus the medial side of a user's right leg is on the left side of the right leg, and the lateral side of a user's right leg is on the right side of the right foot. The medial side of a user's left leg is on the right side of the leg, and the lateral side of a user's left leg is on the left side of the leg.

Figure 3:
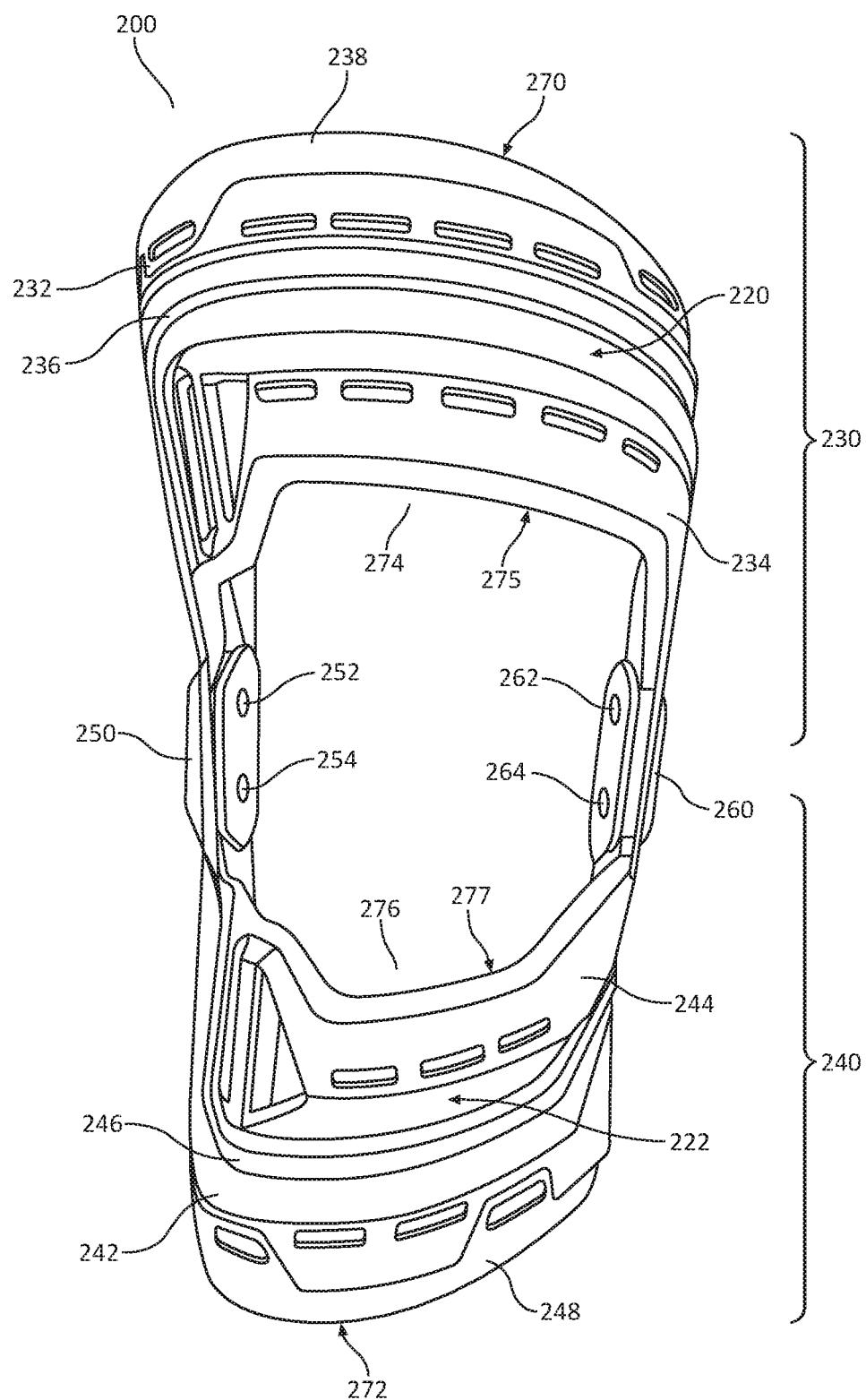
FIG. 3 is a front view of an embodiment of a frame assembly.

FIG. 3 shows a frame assembly 200 from a front view. As shown in FIG. 3, a frame assembly 200 may have a top portion 230 and a bottom portion 240. In some embodiments, the top portion 230 shown in FIG. 3 may correspond to the first portion 212 shown in FIG. 2. In some embodiments, the bottom portion 240 shown in FIG. 3 may correspond to the second portion 214 shown in FIG. 2. The top portion 230 may define an overall outer surface 220, and the bottom portion 240 may define an overall outer surface 222. In some embodiments, the top portion outer surface 220 and bottom portion outer surface 222 may be substantially convex. That is, the top portion outer surface 220 and bottom portion outer surface 222 may have a curved or domed shape.

In some embodiments, the top portion 230 and bottom portion 240 may be connected by a first articulation element 250 and a second articulation element 260. In some embodiments, the first articulation element 250 may be sized, shaped, or molded to be located on the lateral side 70 of a user's leg or knee when worn, as shown in FIG. 2. In some embodiments, the first articulation element 250 may be sized, shaped, or molded to be located on the medial side 80 of a user's leg or knee when worn. In some embodiments, the second articulation element 260 may be sized, shaped, or molded to be located on the medial side 80 of a user's leg or knee when worn, as shown in FIG. 2.

In some embodiments, the top portion 230 may include an outer frame member 232, an inner frame member 234, and a first flex member 236 in between. In some embodiments, the top portion 230 may also have an outer cushioning member 238 that defines an outer edge 270 of the top portion 230. In some embodiments, the top portion 230 may also have an inner cushioning member 274 defining an inner edge 275 of the top portion 230. As used herein, "edge" refers to the side along the outside limit of an object. For example, an outside edge of the top portion 230 may be defined by an edge of the outer cushioning member 238 and on an inside edge may be defined by the inner cushioning member 274.

In some embodiments, the bottom portion 240 may include an outer frame member 242, an inner frame member 244, and a second flex member 246 in between. In some embodiments, the bottom portion 240 may also have an outer cushioning member 248 that defines an outer edge 272 of the bottom portion 240. In some embodiments, the bottom portion 240 may also have an inner cushioning member 276 that defines an inner edge 277 of the bottom portion 240.

As used herein with relation to the first flex member 236 and the second flex member 246, "between" refers to being substantially adjacent to or into the space separating two objects. For example, "between" may refer to being within the space directly separating two objects, and may also refer to being adjacent to the space directly separating two objects. That is an object may be between a first and second location if a direct line from the first location to the second location would contact the object. And an object may between a first and second location if a direct line from the first location to the second location would pass adjacent to the object.

As shown in FIG. 3, the frame assembly first articulation element 250 may contain a first hinge 252 and a second hinge 254, and the second articulation element 260 may contain a first hinge 262 and a second hinge 264. The frame assembly first articulation element 250 and second articulation element 260 may hingedly or pivotally connect or couple the top portion 230 and the bottom portion 240 to each other. That is the top portion 230 may be hingedly connected by the first articulation element first hinge 252 and second articulation element first hinge 262, and the bottom portion 240 may be hingedly connected by the first articulation element second hinge 254 and second articulation element second hinge 264. In this configuration, the top portion 230 and bottom portion 240 may each pivot in relation to the first and second articulation elements 250, 260. The top portion 230 and bottom portion 240 thus may be pivotally hinged and hingedly move in relation to each other similar to a bi-valve shell.

Figure 4:
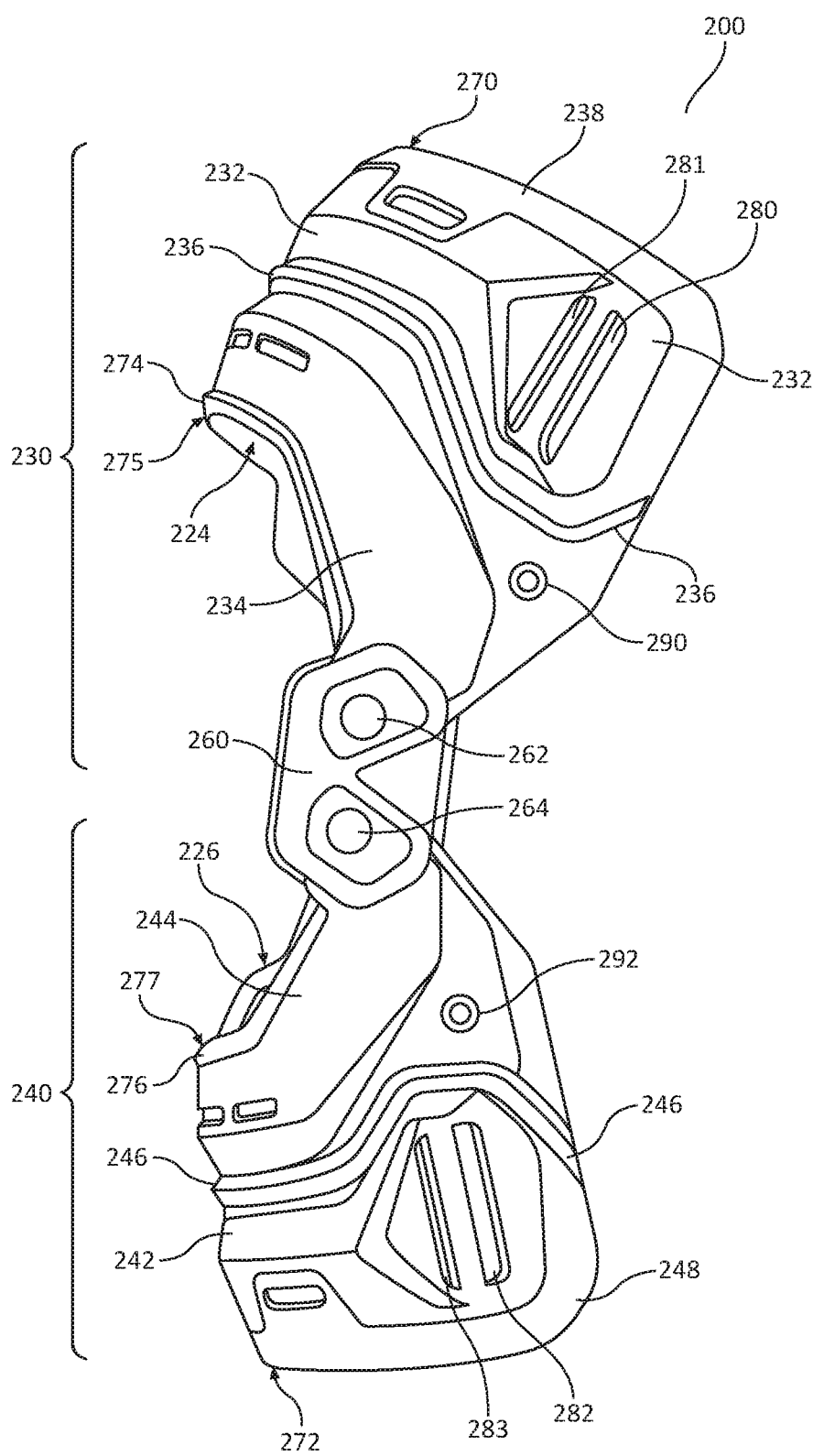
FIG. 4 is a side view of an embodiment of a frame assembly.

FIG. 4 is a side view of an embodiment of the frame assembly 200 showing a top portion 230 and a bottom portion 240. In some embodiments, FIG. 4 may be a view from the medial side 80 of the frame assembly 200. The top portion 230 may define an overall inner surface 224, and the bottom portion 230 may define an overall inner surface 226. In some embodiments, the top portion inner surface 224 and bottom portion inner surface 226 may be substantially concave. That is the top portion inner surface 224 and bottom portion inner surface 226 may have a curved shape. In some embodiments, the top portion inner surface 224 may be curved and shaped to receive the thigh of a user when worn. In some embodiments, the bottom portion inner surface 226 may be curved and shaped to receive a shin of a user when worn.

As shown in FIG. 4, the frame assembly top portion 230 may include the outer frame member 232, the inner frame member 234, and the first flex member 236 in between. The frame assembly top portion 230 also includes the outer cushioning member 238 defining an outer edge 270, and the inner cushioning member 274 defining an inner edge 275. The frame assembly bottom portion 240 may include the outer frame member 242, and inner frame member 244, and a second flex member 246 in between. The frame assembly bottom portion 240 also includes the outer cushioning member 248 defining an outer edge 272 and the inner cushioning member 276 defining an inner edge 277. As shown in FIG. 4, the second articulation 260 includes the first hinge 262 and the second hinge 264.

As shown in FIG. 4, the top portion outer frame member 232 may include first securement loops 280, 281; and the bottom portion outer frame member 242 may include second securement loops 282, 283. This is described further below. In some embodiments, the frame assembly top portion 230 may include a first securement position 290, and the frame assembly bottom portion 240 may also include a second securement position 292, described further below.

Figure 5:
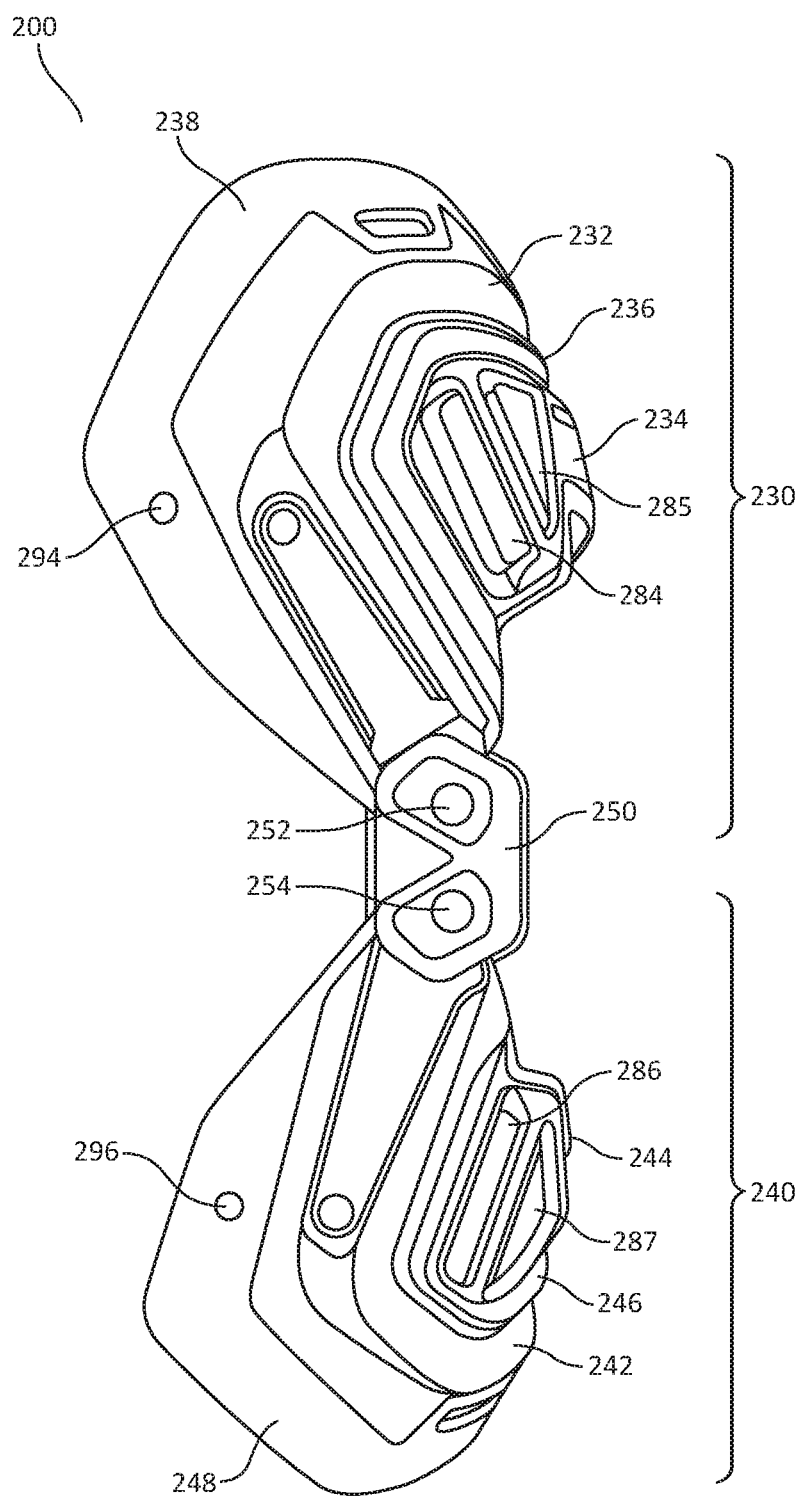
FIG. 5 is a side view of an embodiment of a frame assembly.

FIG. 5 is a side view of an embodiment of the frame assembly 200 showing the top portion 230 and the bottom portion 240. In some embodiments, FIG. 5 may be a view from the lateral side of the frame assembly 200. As shown in FIG. 5, the frame assembly top portion 230 may include the outer frame member 232, the inner frame member 234, and the first flex member 236 in between. The frame assembly top portion 230 also includes the outer cushioning member 238 defining an outer edge 270, and the inner cushioning member 274 defining an inner edge 275. The frame assembly bottom portion 240 may include the outer frame member 242, and inner frame member 244, and the second flex member 246 in between. The frame assembly bottom portion 240 also includes the outer cushioning member 248 which defines an outer edge 272 and the inner cushioning member 276 defining an inner edge 277. As shown in FIG. 5, the first articulation 250 includes the first hinge 252 and second hinge 254.

As shown in FIG. 5, the top portion inner frame member 234 may include third securement loops 284, 285; and the bottom portion inner frame member 244 may include fourth securement loops 286, 287. This is described further below. In some embodiments, the frame assembly top portion 230 may include a third securement position 294, and the frame assembly bottom portion 240 may include a fourth securement position 296, described further below.

Figure 6:
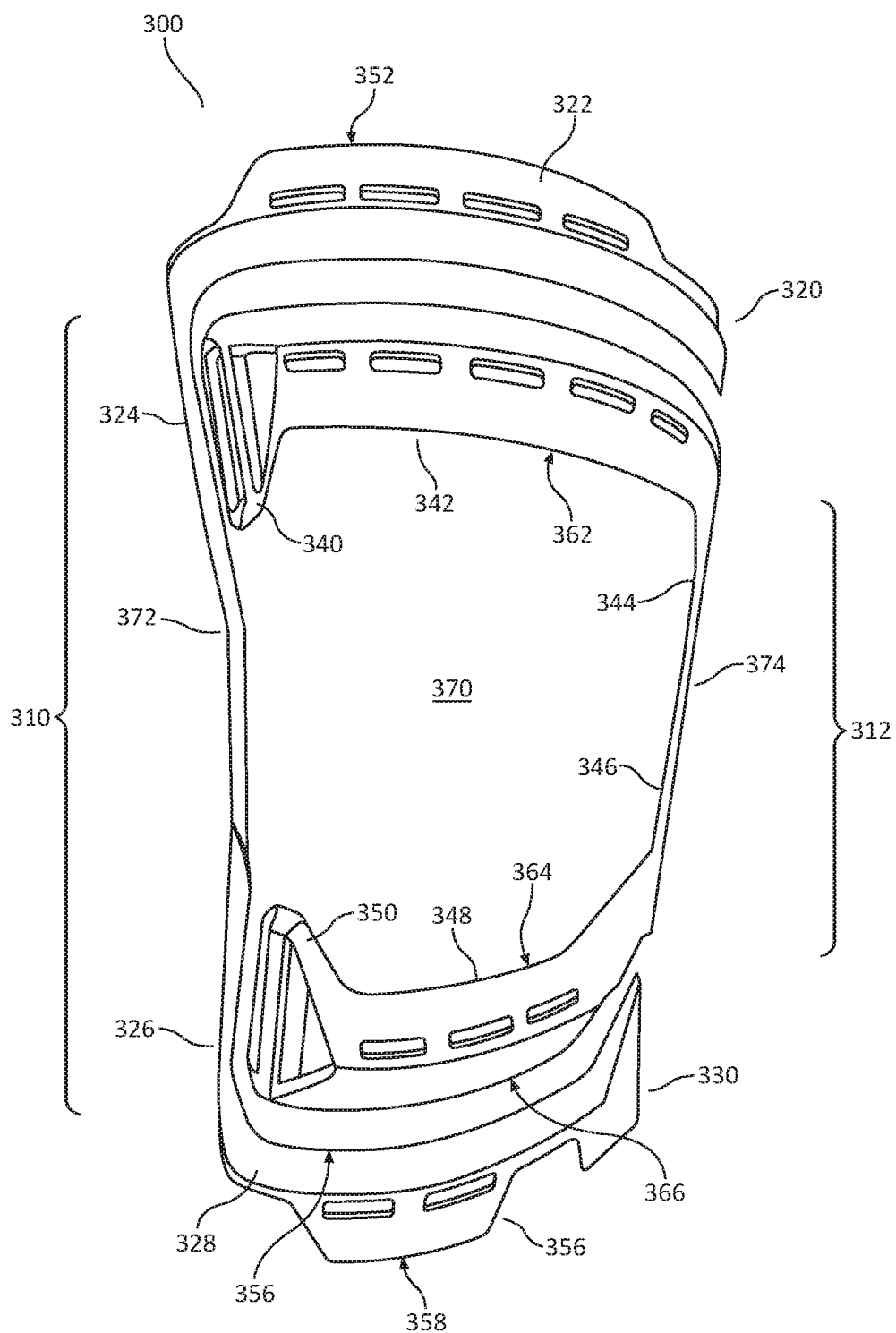
FIG. 6 is a front view of components of an embodiment of a frame assembly.

FIG. 6 is a front view of an embodiment of a support structure 300 that may be included and/or form a portion of the frame assembly 200 shown in FIGS. 3 to 5.

As shown in FIG. 6, the top and bottom portion outer frame members 232, 242 of FIGS. 3 to 5 in combination may form an outer bracket 310. The top and bottom portion inner frame members 234, 244 of FIGS. 3 to 5 in combination may form an inner bracket 312. For example, the outer bracket 310 may include a first side portion 320, a first transverse portion 322 and a second side portion 324 corresponding to the top portion outer frame member 232 shown in FIGS. 3 to 5. The outer bracket 310 may also include a second side portion 326, a second transverse portion 328, and a first side portion 330 corresponding to the bottom portion outer frame member 242 shown in FIGS. 3 to 5. The inner bracket 312 may include a second side portion 340, a first transverse portion 342, and a first side portion 344 corresponding to the top portion inner frame member 234 shown in FIGS. 3 to 5. The inner bracket may also include a first side portion 346, a second transverse member 348, and a second side portion 350 corresponding to the bottom portion inner frame member 244 shown in FIGS. 3 to 5.

As shown in FIG. 6, the outer bracket 310 may define a first outer edge 352, a first inner edge 354, a second inner edge 356, and a second outer edge 358. The inner bracket 312 may define a first outer edge 360, a first inner edge 362 a second inner edge 364, and a second outer edge 366. The outer bracket 310 may define a substantially C-shaped structure. That is the outer bracket 310 may define a curve having an opening. The inner bracket 312 may define a substantially C-shaped structure. That is the inner bracket 312 may define a curve having an opening. As shown in FIG. 6, the outer bracket 310 and inner bracket 312 are arranged with the outer bracket 310 opening arranged in the opposite direction as the inner bracket 312 opening. It is envisioned that the outer bracket 310 and inner bracket 312 may be arranged with openings facing in a direction opposite that shown in FIG. 6. The outer bracket 310 may have an opening pointed to either the lateral or medial side of a user, and the inner bracket 312 may have an opening pointed to either the lateral or medial side of user. The outer bracket 310 and inner bracket 312 may define a central opening 370 sized to receive a knee of a user when worn. The outer bracket 310 may include a first articulation point 372 for locating an articulation (for example, the first articulation 350 shown in FIGS. 3 to 5) to allow the outer bracket 310 to form a top and bottom portion that can hingedly pivot in relation to one another. The inner bracket 312 may include a second articulation point 374 for locating an articulation (for example, the second articulation 260 shown in FIGS. 3 to 5) to allow the inner bracket 312 to form a top and bottom portion that can hingedly pivot in relation to one another.

As used herein, "edge" refers to the side along the outside limit of an object. For example, the edge of the outer bracket 310 may be defined on the outside by a first outer edge 352 and a second outer edge 358. The edge of the outer bracket 310 may be defined on the inside by a first inner edge 354 and a second inner edge 356. The edge of the inner bracket 312 may be defined on the outside by a first outer edge 360 and a second outer edge 366. The edge of the inner bracket 312 may be defined on the inside by a first inner edge 362 and a second inner edge 364.

In some embodiments, the outer bracket 310 may be joined to the inner bracket 312 along at least a portion of the length of the outer bracket 310 and the inner bracket 312. For example, the outer bracket 310 may be joined to the inner bracket 312 by joining the outer bracket first inner edge 354 to the inner bracket first outer edge 360 by attaching a first flex member (for example, the first flex member 236 of FIGS. 3 to 5). For example, a first flex member may be attached along at least a portion of the length of the outer bracket first side portion 320, first transverse portion 322, and second side portion 324 corresponding to the top portion outer frame member 232 shown in FIGS. 3 to 5. The first flex member may also be attached along at least a portion of the length of the inner bracket second side portion 340, first transverse portion 342, and first side portion 344 corresponding to the top portion inner frame member 234 shown in FIGS. 3 to 5.

Additionally or alternatively, the outer bracket 310 may be joined to the inner bracket 312 by joining the outer bracket second inner edge 356 to the inner bracket second outer edge 366 by attaching a second flex member (for example, the second flex member 246 of FIGS. 3 to 5). For example, a second flex member may be attached along at least a portion of the length of the outer bracket second side portion 326, second transverse portion 328, and first side portion 330 corresponding to the bottom portion outer frame member 242 shown in FIGS. 3 to 5. The second flex member may also be attached along at least a portion of the length of the inner bracket a first side portion 346, second transverse member 348, and second side portion 350 corresponding to the bottom portion inner frame member 244 shown in FIGS. 3 to 5.

In some embodiments, a first flex member may have a first side attached along at least a portion of the length of the outer bracket 310, for example along the outer bracket first inner edge 354, and the first flex member may have a second side attached along at least a portion of the length of the inner bracket 312, for example along the inner bracket first outer edge 360. Additionally or alternatively, a second flex member may have a first side attached along at least a portion of the length of the outer bracket second inner edge 356 and a second side attached along at least a portion of the length of the inner bracket second outer edge 366.

In some embodiments, the outer bracket first outer edge 352 may be attached to a cushioning member (such as the top portion outer cushioning member 238 shown in FIGS. 3 to 5). The outer bracket second outer edge 358 may also be attached to a cushioning member (such as the bottom portion outer cushioning member 248 shown in FIGS. 3 to 5). The inner bracket first inner edge 362 may be attached to a cushioning member (such as the top portion inner cushioning member 274 shown in FIGS. 3 to 5). The inner bracket second inner edge 364 may be attached to a cushioning member (such as the bottom portion inner cushioning member 276 shown in FIGS. 3 to 5).

In some embodiments, the outer and inner brackets 310, 312 may be made from a rigid material that is substantially weight bearing. That is the outer and inner brackets 310, 312 may be formed to bear weight without deforming or bending. For example, the outer and inner brackets 310, 312 may be formed from material such as metal, plastic, wood, fiberglass, or a synthetic fiber composite such as that sold under the trade name Kevlar®. In some embodiments the outer and inner brackets 310, 312 may be formed from material that is weight bearing yet is also flexible or pliable. For example, the outer and inner brackets 310, 312 may be formed from a polymer such as plastic or hard rubber that may deform when subjected to certain pressures, yet is resilient enough to maintain a suitable shape. The outer and inner brackets 310, 312 may be formed from a material that can be formed using available forming methods such as injection molding or shape molding, for example a thermoplastic elastomer, or thermoplastic rubber. In some embodiments, the outer and inner bracket 310, 312 may be each made from the same material or from different material to provide a suitable fit or feel to a user when worn.

Figure 7:
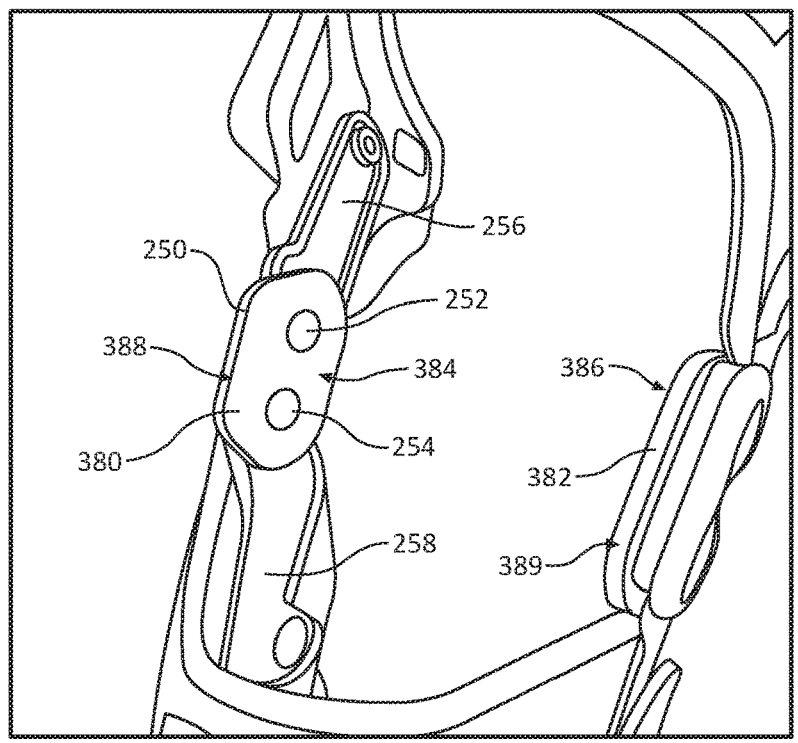
FIG. 7 is a side view of components of an embodiment of a frame assembly.
Figure 8:
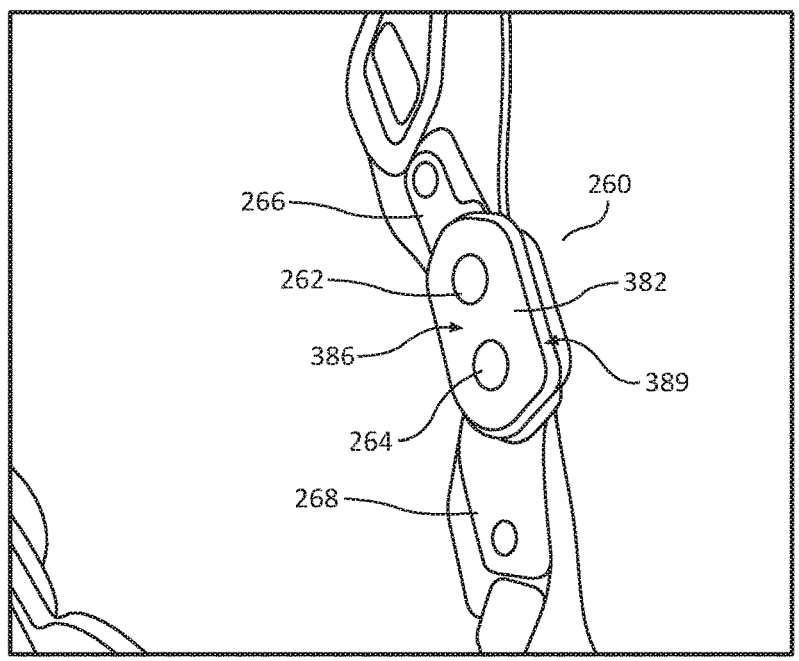
FIG. 8 is a side view of components of an embodiment of a frame assembly.

FIGS. 7 and 8 are side views of an embodiment of the frame assembly 200 shown in FIGS. 3 to 5 to illustrate certain features of the first and second articulation elements 250 and 260. As shown in FIG. 7, the first articulation element 250 includes the first articulation element first hinge 252 and second hinge 254. As shown in FIG. 8, the second articulation element 260 includes the second articulation element first hinge 262 and second hinge 264. In some embodiments, the first and second articulation elements 250, 260 may be a plate or flat material shaped with an inner surface 384, 386 that are configured to face toward the leg of a user. In some embodiments the first articulation element inner surface 384 and second articulation element inner surface 386 may each be shaped with a complementary fit to the side of a user's knee.

As shown in FIGS. 7 and 8, in some embodiments, the first articulation element inner surface 384 and second articulation element inner surface 386 may have recessed holes for receiving the first hinges 252, 262 and the second hinges 254, 264. The first and second articulation elements 250, 260 may also include an over molding 380, 382 that defines the inner surfaces 384, 386. For example, the first and second articulation elements overmolding 380, 382 may be attached to the first and second articulation elements 250, 260 and be configured to face the leg of a user when worn. The overmolding 380, 382 may be formed to cover the first and second articulation elements 250, 260 and define edges 388, 389 that extend wider than the first and second articulation elements 250, 260. In some embodiments, the overmolding 380, 382 may be formed from a pliable or resilient material such that the overmolding edges 388, 389 curve over or around a portion of the first and second articulation elements 250, 260. In some embodiments, the overmolding 380, 382 may be formed from a pliable or resilient material to provide a comfortable fit when the frame assembly 200 is worn by a user. In some embodiments, the second articulation element 260 may be sized, shaped, or molded to be located on the lateral side 70 of a user's leg or knee when worn.

In some embodiments, the first and second articulation elements 250, 260 may be formed from rigid materials such as plastic or metal. For example, the first and second articulation elements 250, 260 may be formed from aluminum or steel. The first and second articulation elements 250, 260 may include dual-axis geared hinges. A dual axis geared hinge design allows for a natural full range of motion and may incorporate a hyperextension stopping point integrated in the geometry of the hinge gearing which helps reduce the potential risk of the joint from passing beyond a point of extension where the risk of injury is amplified. For example, the first and second articulation elements 250, 260 may include a hyperextension stopping point that does not allow the knee of a user to hyperextend more than 15, 10, or 5 degrees. The inside of the hinge may be over molded with flexible, soft feeling thermoplastic material for a comfortable fit.

In some embodiments, the frame assembly 200 may include hinge stays 256, 258, 266, 268 to attach the first and second articulation elements 250, 260 to the frame assembly 200. For example first hinge stays 256, 258 may be used to attach the first articulation element 250 to the frame assembly 200. Second hinges stays 266, 268 may be used to attach the second articulation element 260 to the frame assembly 200. In some embodiments, the hinge stays 256, 258,266, 268 may be formed at an offset angle from each other to provide particular stopping point for the first hinges 252, 262 and the second hinges 254, 264. The hinge stays 256, 258, 266, 268 may be formed of a right material such as metal or plastic. In some embodiments hinge stays 256, 258,266, 268 may be formed from tempered aluminum. The rigid tempered aluminum hinge stays may be specially designed for the support & alignment requirements of the frame assembly lateral and medial sides and securely fixed with the frame assembly 200, providing a reduction in the torsional forces on a user's joint when worn.

Figure 9A:
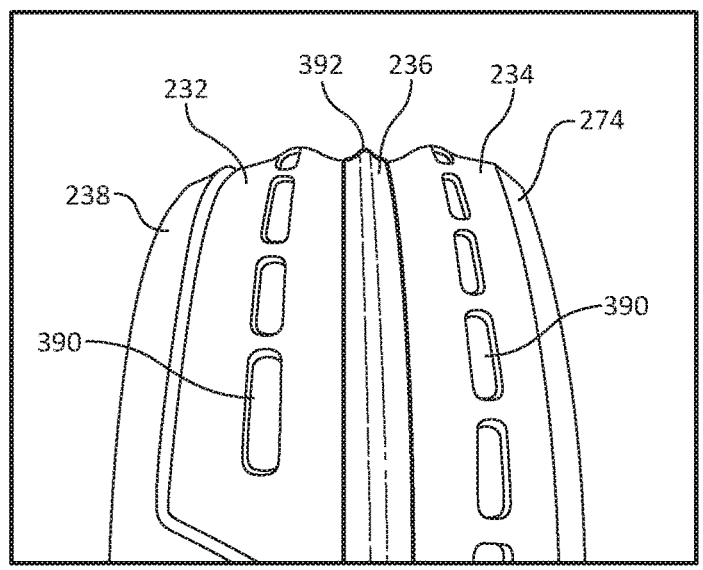
FIGS. 9A-9C are side views of components of an embodiment of a frame assembly.
Figure 9B:
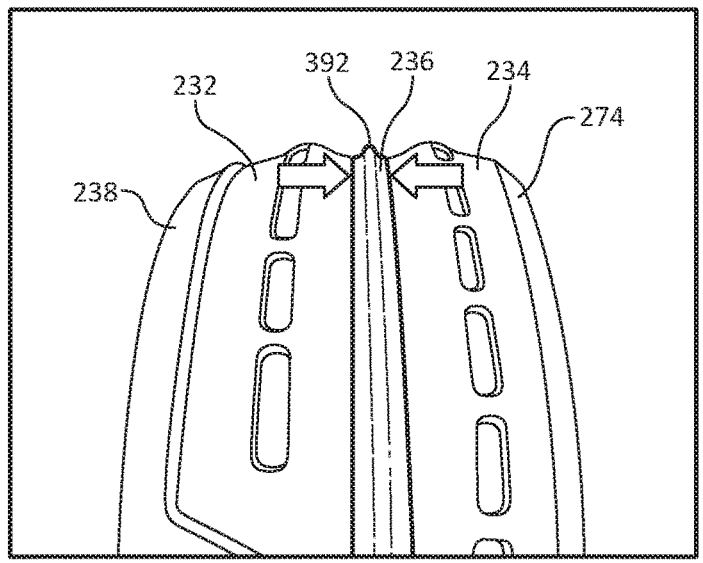
Figure 9C:
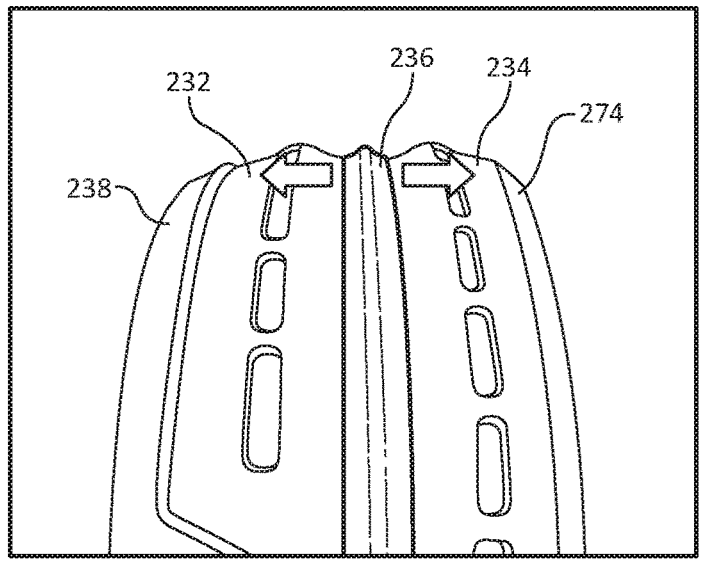

FIGS. 9A-9C illustrate an embodiment of the frame assembly 200 shown in FIGS. 3 to 5 to illustrate certain features of the first and second flex members 236, 246. Reference is made to the features of the top portion 230 shown in FIGS. 3 to 5, however, the same features may apply to similar elements of the bottom portion 240. As shown in FIG. 9A, the first flex member 236 may be attached to the outer frame member 232 and inner frame member 234. The outer frame member 232 may be attached to the outer cushioning member 238, and the inner frame member 234 may be attached to the inner cushioning member 274. As shown in FIG. 9A, the outer frame member 232 and inner frame member 234 may each define holes 390. In some embodiments, the holes 390 may allow ventilation for user when worn. In some embodiments, the holes 390 may allow an outer frame member 232 and inner frame member 234 to be made with less material.

In some embodiments, the first and second flex members 236, 246 may be made from pliable or flexible material that may deform or bend when subjected to external forces. For example, as shown in FIG. 9B, the first flex member 236 may be pliable or flexible to allow the first flex member 236 to compress or retract when subjected to a force in the direction of the two arrows. The force may be directed in the direction of the two arrows by pressure on the outer frame member 232 or the inner frame member 234. A pliable or flexible material may allow the first flex member to act as a bumper or shock absorber. A pliable or flexible material may also allow the outer frame member 232 and inner frame member 234 to move relative to one another and create a fit that is suitable for the size and shape of a user's leg when worn.

In some embodiments, the first and second flex members 236, 246 may be made from resilient or elastic material that may retract or reform into an original shape when a force is released. For example, as shown in FIG. 9C, the first flex member 236 may be resilient or elastic to retract or reverse into an original shape in the direction of the arrows. For example, a force may be first applied in the direction of the arrows in FIG. 9B. When the force is released, the first flex member 236 may retract into its original shape in the direction of the arrows in FIG. 9C. In some embodiments, the first flex member 236 may include a ridge 392 to bias the first flex member 236 in a direction when compressed and provides added shock absorbing capability. In some embodiments, the first and second flex members 236, 246 may be made from material such as rubber or a polymer that is pliable and flexible. In some embodiments, the outer cushioning member 238 and inner cushioning member 274 may be made from the same material as the first flex member 236.

In some embodiments, the knee brace assembly 110 may include a device for attaching the frame assembly 200 to the leg of a user. In some embodiments, a sleeve may be used as a securement system for covering the frame assembly 200 and keeping the frame assembly 200 secured to a user's leg. In some embodiments, the securement system may secure the frame assembly 200 to the leg of a user by wrapping around the frame assembly 200 and the user's leg. In some embodiments, the securement system may include a strap arrangement 210 such as those shown in FIG. 10. For example, a strap arrangement 210 may include straps or harnesses that secure portions of the frame assembly 200 against a user's leg when worn and allow the frame assembly 200 to pivot, hinge, or move with the user's leg.

Figure 10:
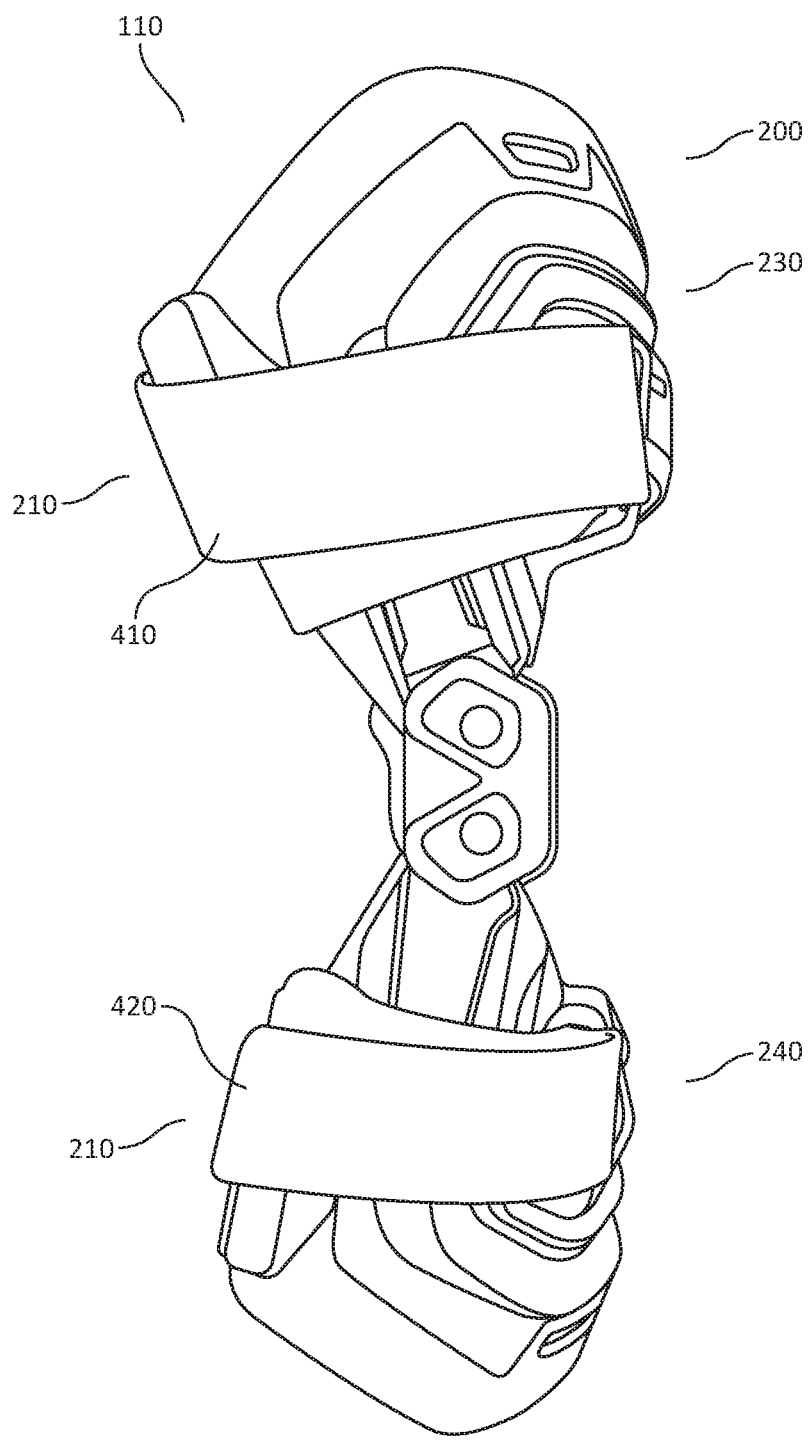
FIG. 10 is a side view of an embodiment of a knee brace assembly.

FIG. 10 is a side view of the knee brace assembly 110 showing the frame assembly 200 and strap arrangement 210 of FIG. 2, to illustrate additional features. As shown in FIG. 10, the strap arrangement 210 may include straps for retaining the frame assembly 200 against the leg of a user when worn. For example, the strap arrangement 210 may comprise at least a first strap 410 and a second strap 420. The first strap 410 may be used to retain the top portion 230 of the frame assembly 200 against the thigh of a user when worn. The second strap 420 may be used to retain the bottom portion 240 of the frame assembly 200 against the shin of a user when worn.

Figure 11:
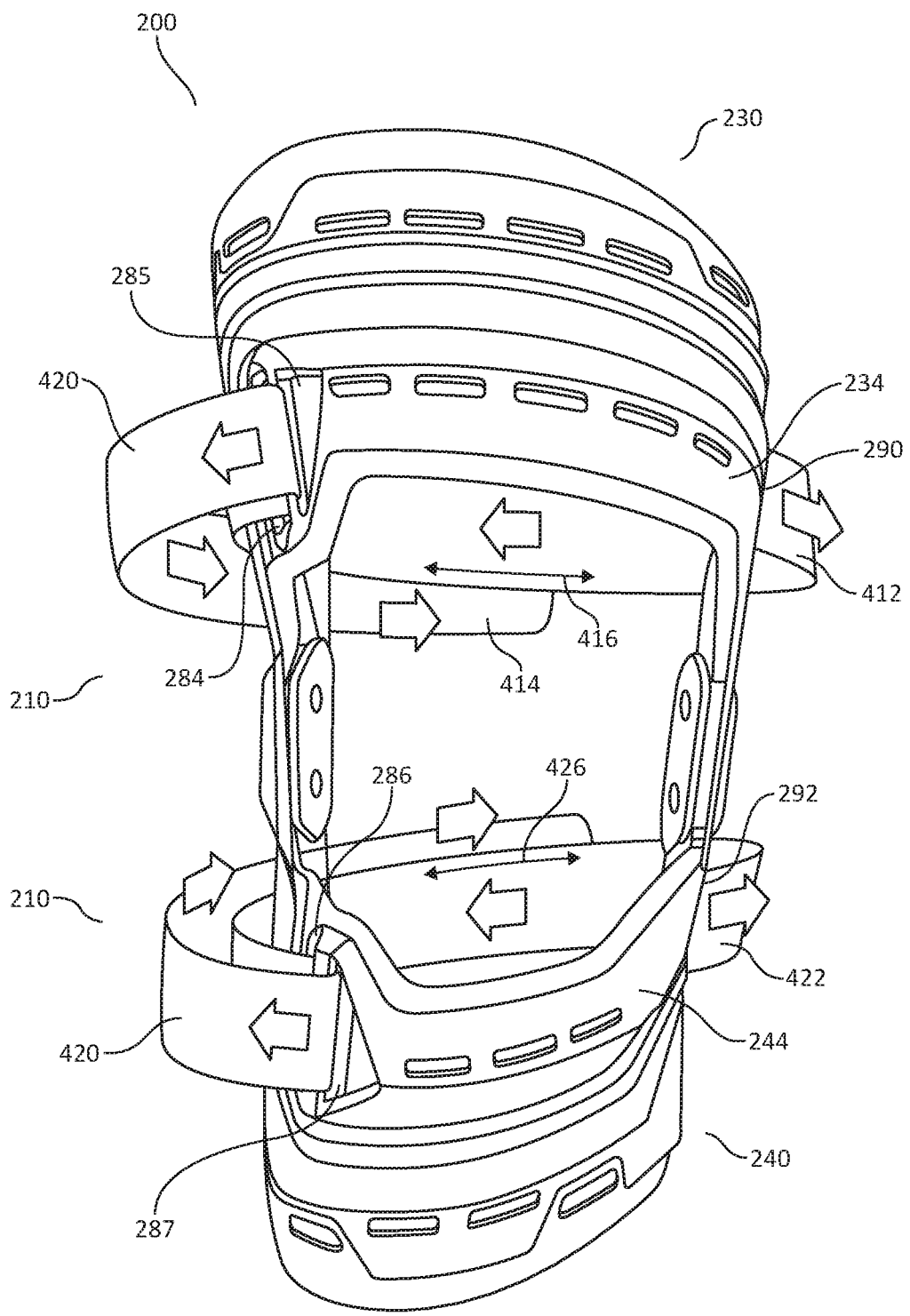
FIG. 11 is a front view of an embodiment of a knee brace assembly.

FIG. 11 is a front view of the knee brace assembly 110 showing additional features of the frame assembly 200 and strap arrangement 210. As shown in FIG. 11, the frame assembly 200 may be joined to the strap arrangement 210 via the first securement position 290 and the second securement position 292.

For example, the strap assembly first strap 410 may have a first end 412, a second end 414, and a length in between 416. In some embodiments, the first strap first end 412 may be attached to the frame assembly top portion 230 at the first securement position 290. The first strap second end 414 may be fed through the top portion third securement loops 284, 285 and folded back to contact the length 416 of the first strap 410. For example, the length 416 of the first strap 410 may include a fastener, such as a snap fit or a hook and loop fastener such as Velcro®, to attach the first strap second end 414 along the length 416 of the first strap 410.

In some embodiments, the strap assembly second strap 420 may have a first end 422, a second end 424, and a length in between 426. In some embodiments, the second strap first end 422 may be attached to the frame assembly bottom portion 240 at the second securement position 292. The second strap second end 424 may be fed through the bottom portion fourth securement loops 286, 287 and folded back to contact the length 426 of the first strap 420. For example, the length 426 of the second strap 420 may include a fastener, such as a snap fit or a hook and loop fastener such as Velcro®, to attach the second strap second end 424 along the length 426 of the second strap 420. Using the first and second straps 410, 420 in this configuration may secure the top portion inner frame member 234 against the thigh of a user when worn, and the bottom portion inner frame member 244 against the shin of a user when worn.

Figure 12:
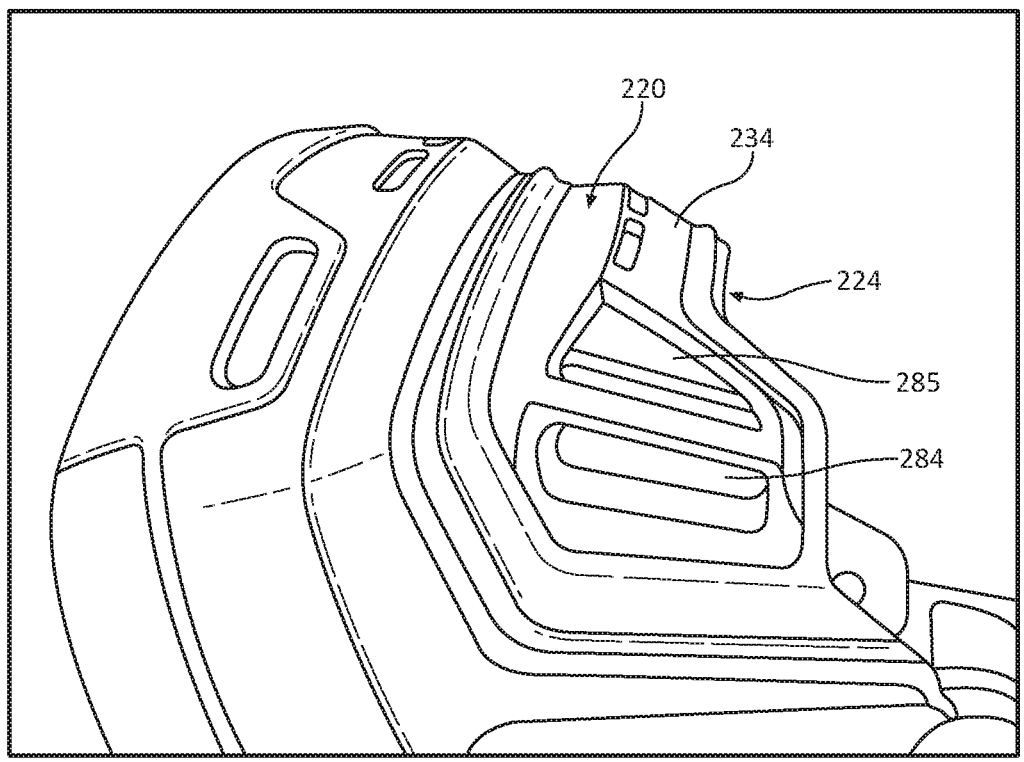
FIG. 12 is a side view of components of an embodiment of a frame assembly.
Figure 13:
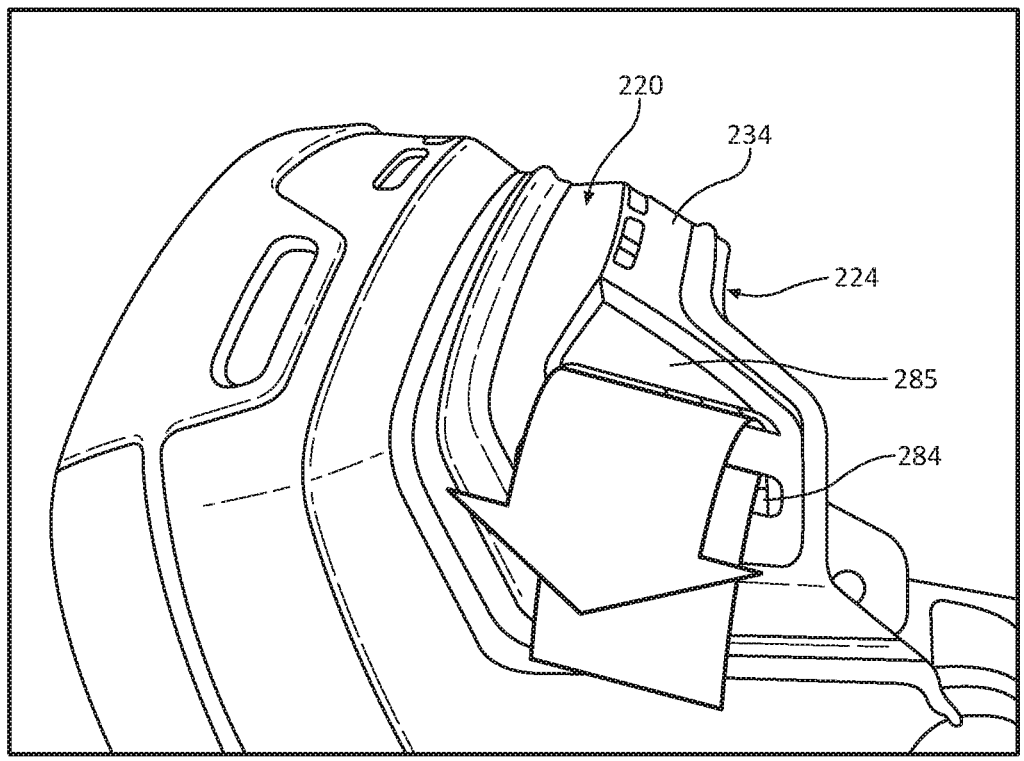
FIG. 13 is a side view of components of an embodiment of a frame assembly.

As shown in FIGS. 12 and 13, the frame assembly top portion 230 may have structural elements integrally formed to receive the first strap 410. In some embodiments, the frame assembly 200 may have multiple structural elements to receive a strap arrangement 210 having straps or belts. Reference will be made in FIGS. 12 and 13, with description to the top portion inner frame member 234, however it to be understood that this description may also describe additional elements located on the top portion outer frame member 232, and bottom portion outer and inner frame member 234 disclosed in FIGS. 4 and 5.

As shown in FIG. 12, the top portion inner frame member 234 includes the third securement loops 284, 285. The securement loops 284, 285 may include holes or spaces from the top portion outer surface 220 through to the top portion inner surface 224. As shown in FIG. 13, a strap may be attached to the top portion inner frame member 234 by threading a strap through securement loops 284, 285 in the path shown by the arrow. For example, the first strap second end 414 may be passed or threaded through the securement loop 284, 285 and doubled back.

Figure 14:
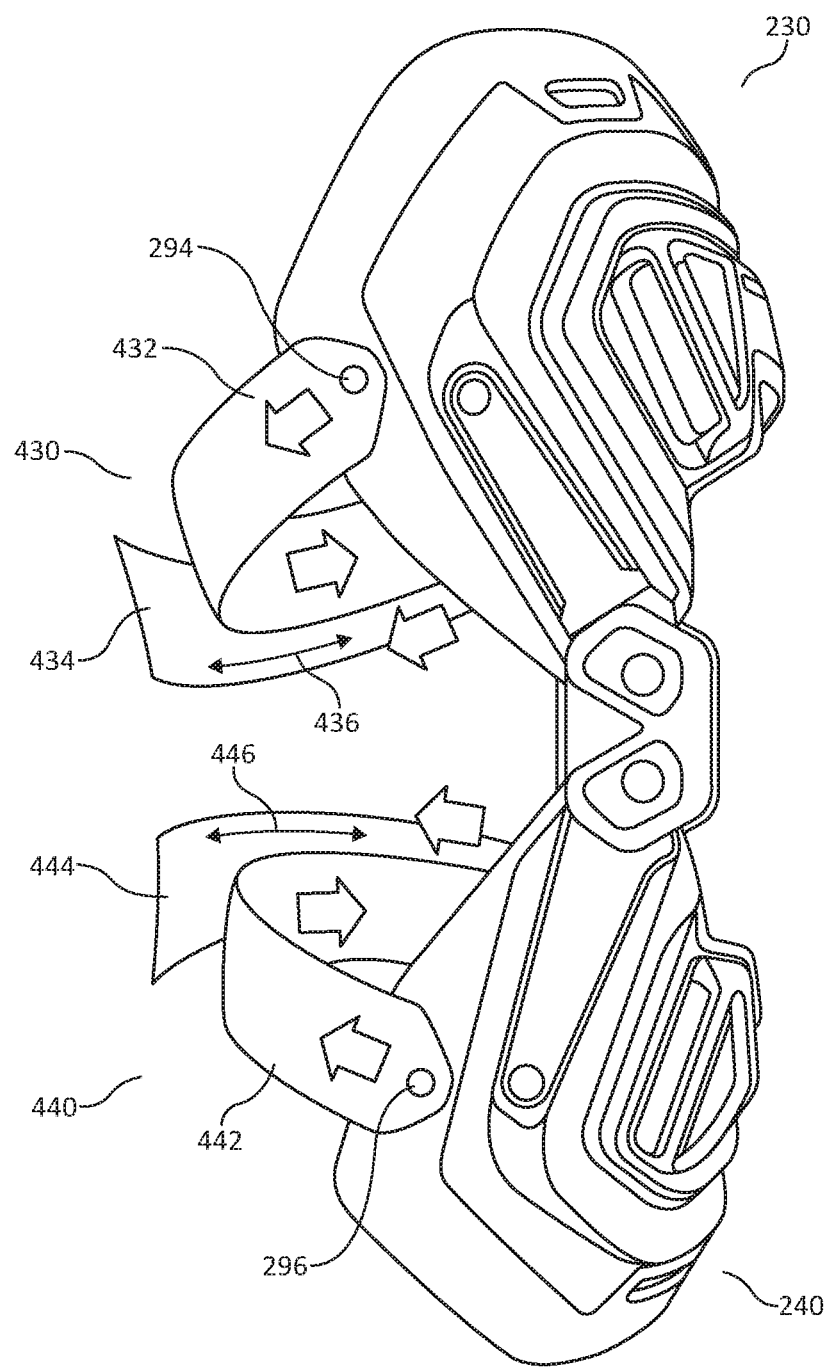
FIG. 14 is a side view of an embodiment of a knee brace assembly.
Figure 15:
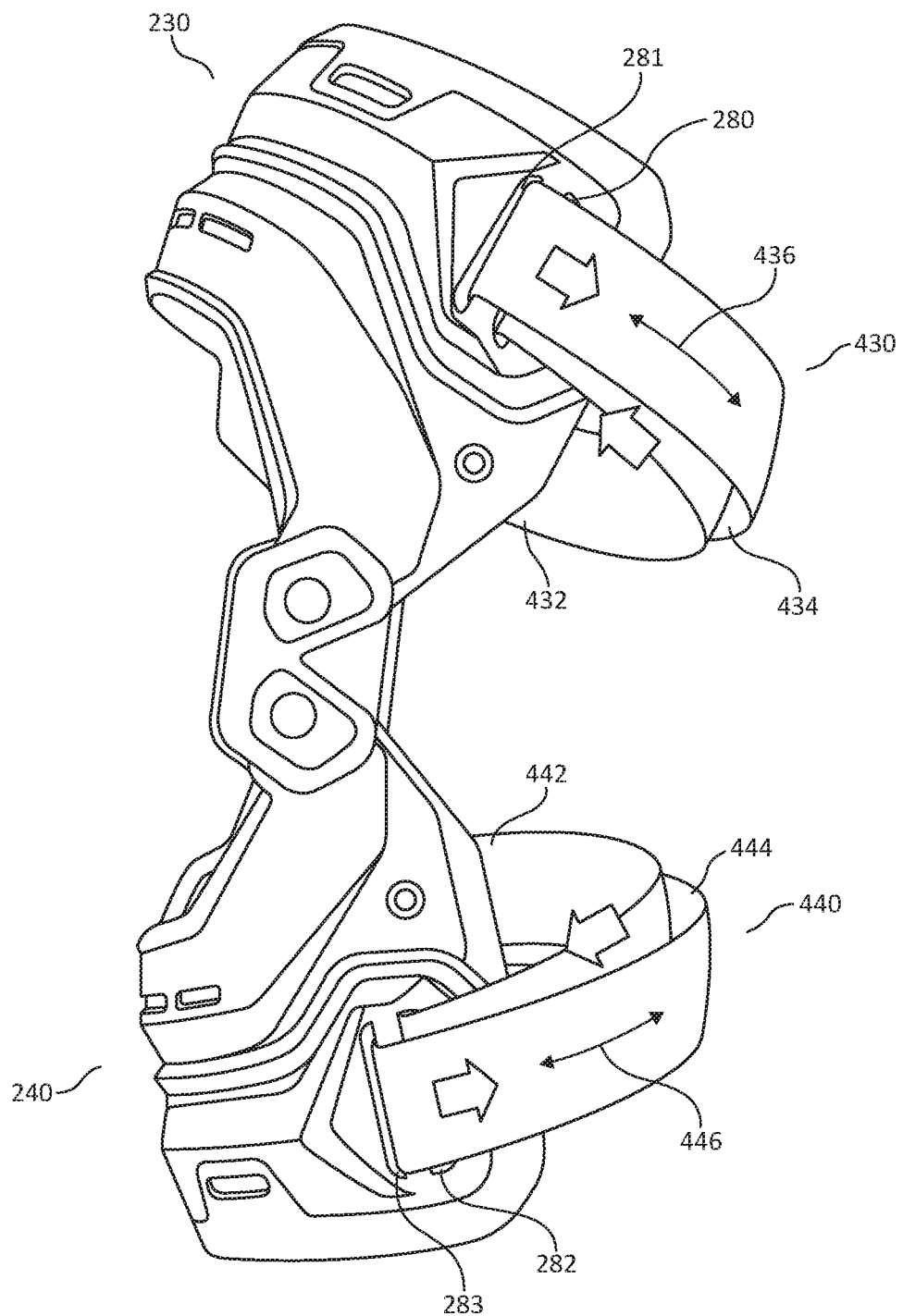
FIG. 15 is a side view of an embodiment of a knee brace assembly.

In some embodiments, the top and bottom portions 230, 240 of the frame assembly 200 may be secured to the leg of a user using a similar securement system such as a strap arrangement 210 as previously described. As shown in FIGS. 14 and 15, a third strap 430 may be used to secure the top portion 230 of the frame assembly 200 to a user's thigh, and a fourth strap 440 may be used to secure the bottom portion 240 of the frame assembly 200 to a user's shin. For example, the third strap 430 may have a first end 432, a second end 434, and a length 436 in between. The third strap 430 may have the first end 432 attached to the third securement position 294. The third strap second end 434 may be fed through the top portion outer frame member first securement loops 280, 281 and overlapped with the third strap length 436. The length 436 of the third strap 430 may include a fastener (not shown), such as a snap fit or a hook and loop fastener such as Velcro®, to attach the third strap second end 434 along the length 436 of the third strap 430 to keep it in place.

As shown in FIGS. 14 and 15, a fourth strap 440 may be used to secure the bottom portion 240 of the frame assembly 200 to a user's shin. For example, the fourth strap 440 may have a first end 442, a second end 444, and a length 446 in between. The fourth strap 440 may have the first end 442 attached to the fourth securement position 296. The fourth strap second end 444 may be fed through the bottom portion outer frame member second securement loops 282, 283 and overlapped with the fourth strap length 446. The length 446 of the fourth strap 440 may include a fastener (not shown), such as a snap fit or a hook and loop fastener such as Velcro®, to attach the fourth strap second end 444 along the length 446 of the fourth strap 440 to keep it in place.

Figure 16:
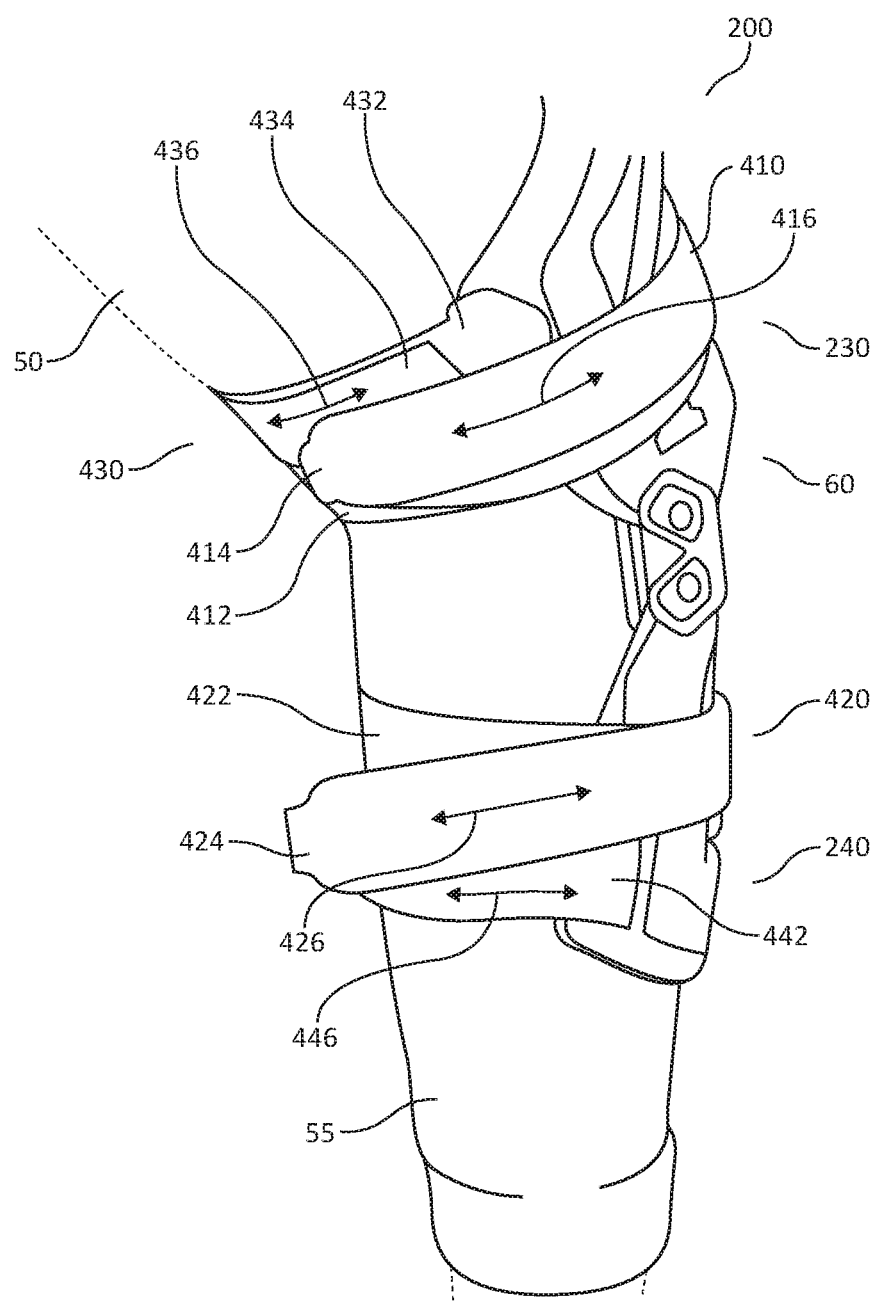
FIG. 16 is a rear perspective view of an embodiment of a knee brace assembly when worn.

FIG. 16 is a rear view of the frame assembly 200 when worn by a user. As shown in FIG. 16 the frame assembly 200 may be worn by a user by placing the top portion 230 over the user's thigh and the bottom portion 240 over the user's shin 55. The frame assembly 200 may be positioned to be worn to support the user's knee 60. In some embodiments, after the frame assembly 200 is in position, a securement system such as a sleeve or strap may be placed over the frame assembly 200 to hold it in position against the user's leg when worn.

In some embodiments, the top portion 230 may be attached to the user's thigh by attaching the first end 432 of the third strap 430 to the frame assembly 200, and passing the third strap length 436 behind the user's thigh 50. The second end 434 is passed through the securement loops (shown in FIG. 4) and folded back over to attach to the third strap length 436. After attaching the third strap 430, the first strap 410 may be secured to the user's thigh 50 by attaching it over the third strap 430. The first end 412 of the first strap 410 may be attached to the frame assembly top portion 230 and the length 416 of the first strap 410 is passed behind the user's thigh 50. The second end 414 of the first strap 410 is passed through the securement loops (shown in FIG. 5) and folded back over to attach to the first strap length 416.

In some embodiments, the bottom portion 240 may be attached to the user's shin by attaching the first end 442 of the fourth strap 440 to the frame assembly 200, and passing the fourth strap length 446 behind the user's shin 55. The second end 444 (hidden from view) is passed through the securement loops (shown in FIG. 4) and folded back over to attach to the fourth strap length 446. After attaching the fourth strap 440, the second strap 420 may be secured to the user's shin 55 by attaching it over the fourth strap 440. The first end 422 of the second strap 420 may be attached to the frame assembly bottom portion 240 and the length 426 of the second strap 420 is passed behind the user's shin 52. The second end 424 of the second strap 420 is passed through the securement loops (shown in FIG. 5) and folded back over to attach to the second strap length 426.

Figure 17:
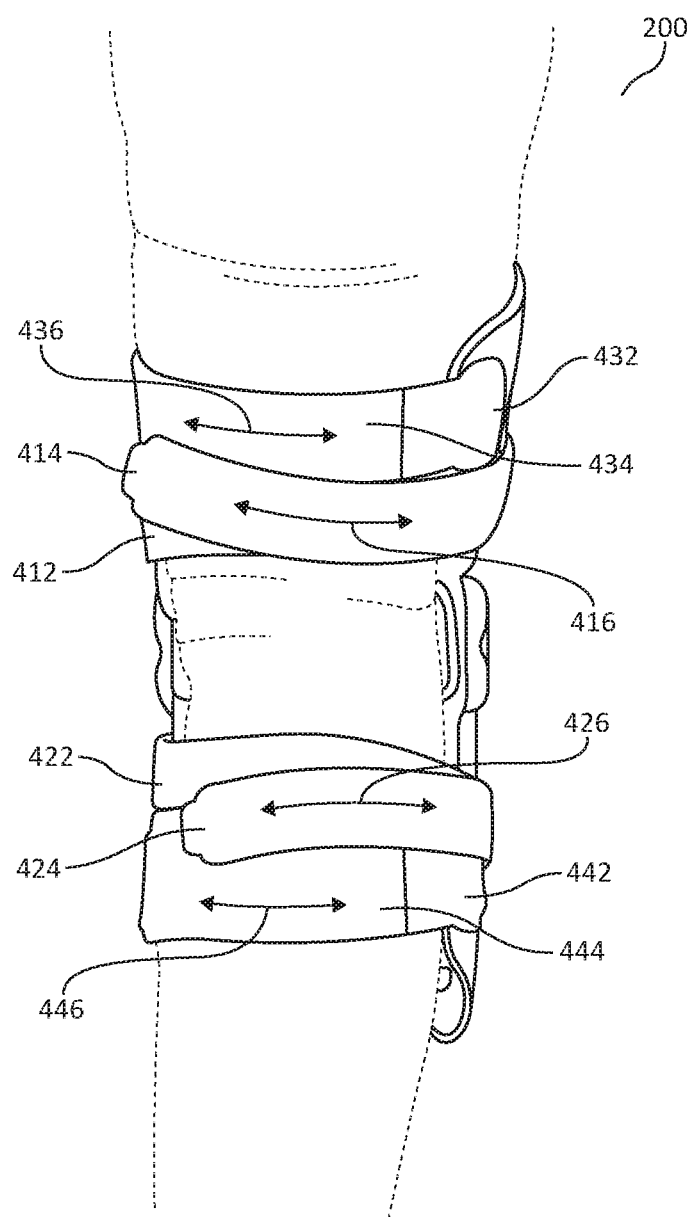
FIG. 17 is a rear view of an embodiment of a knee brace assembly when worn.

It is envisioned, that the third and first straps 430, 410 may be attached to each other, for example by having similar attachment mechanism on both the third and first straps 430, 410. It is also envisioned, that the second and fourth straps 420, 440 may be attached to each other, for example by having similar attachment mechanism on both the second and fourth straps 420, 440. For example, as shown in FIG. 17, the first and third second strap ends 414, 434 may each have one of a hook or loop from a hook and loop device such as Velcro®. The first and third strap lengths 416, 436 may have a corresponding hook or loop. In this manner, the first strap second end 414 may be attached to either of the first or third strap lengths 416, 436. Similarly, the third strap second end 434 may be attached to either of the first or third strap lengths 416, 436.

As shown in FIG. 17, the second and fourth second strap ends 424, 444 may each have one of a hook or loop from a hook and loop device such as Velcro®. In some embodiments, the first, second, third, and fourth straps 410, 420, 430, 440 may be color coded to guide a proper securement position or securement assembly sequence. In the some embodiments, the first and third strap 410, 430 may be connected to each other to provide a unitary fit. In some embodiments, the second and fourth strap 420, 440 may be connected to each other to provide a unitary fit. The second and fourth strap lengths 426, 446 may have a corresponding hook or loop. In this manner, the second strap second end 424 may be attached to either of the second or fourth strap lengths 426, 446. Similarly, the fourth strap second end 444 may be attached to either of the second or fourth strap lengths 426, 446.

Figure 18:
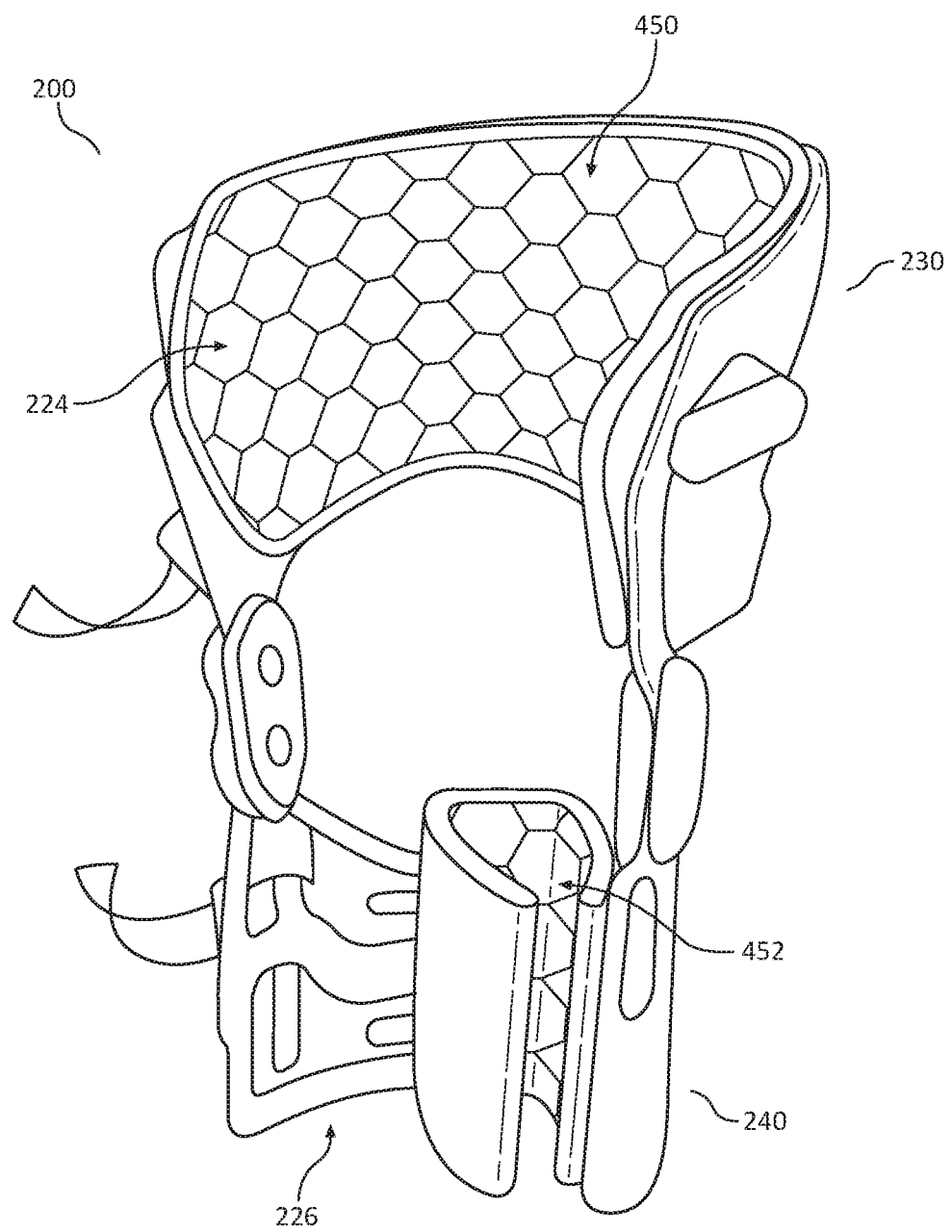
FIG. 18 is a rear view of an embodiment of a knee brace assembly.

FIG. 18 is a rear view of the frame assembly 200 to illustrate an additional embodiment. As shown in FIG. 16, the frame assembly 200 top portion 230 may have an inner surface 224 and the bottom portion 240 may have an inner surface 226. In some embodiments, the top and bottom portion inner surfaces 224, 226 may be relatively curved. In some embodiments, the top portion inner surface 224 may be curved with a concave shape to receive the thigh of a user. In some embodiments, the bottom portion inner surface 226 may be curved with a concave shape to receive the shin of a user. As shown in FIG. 18, the frame member may include padding 450,452 such as that shown on the top and bottom inner surfaces 224, 226. The padding 450, 452 may provide additional comfort or fit for the leg of a user when the frame assembly 200 is worn. The padding may be flexible or bendable to comply with the shape of the inner surfaces 224, 226 of the top and bottom portions 230, 240. As shown in FIG. 18, the padding may be removable, as the bottom padding 452 is shown partially removed. Being removable may allow a user to remove the padding 450 and 452 to be washed or exchanged.

Figure 19:
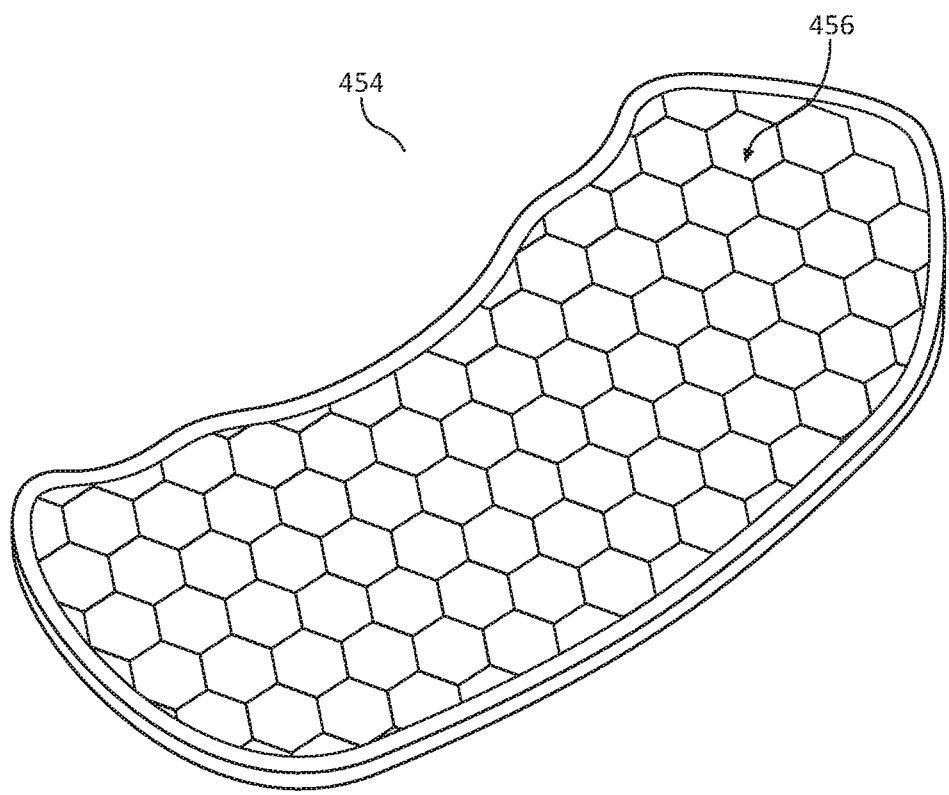
FIG. 19 is a schematic view showing an embodiment of padding that may be used in a knee brace assembly.

FIG. 19 contains an embodiment of padding 454 that may be used with the frame assembly 200. The padding 454 may have an inner surface 456 that is designed to face the leg of a user when worn. The inner surface 456 of the padding may be constructed with a pattern, such as a triangular or diamond pattern that is repeated to create an overall pattern. The pattern used may be one that is suitable for the padding material to be bent or curved to fit within a frame assembly 200 without breaking.

Sleeve Assembly

In some embodiments, the knee brace assembly 110 described in FIGS. 2 to 18 may be used with a sleeve assembly 120, such as shown in FIG. 1.

Figure 20:
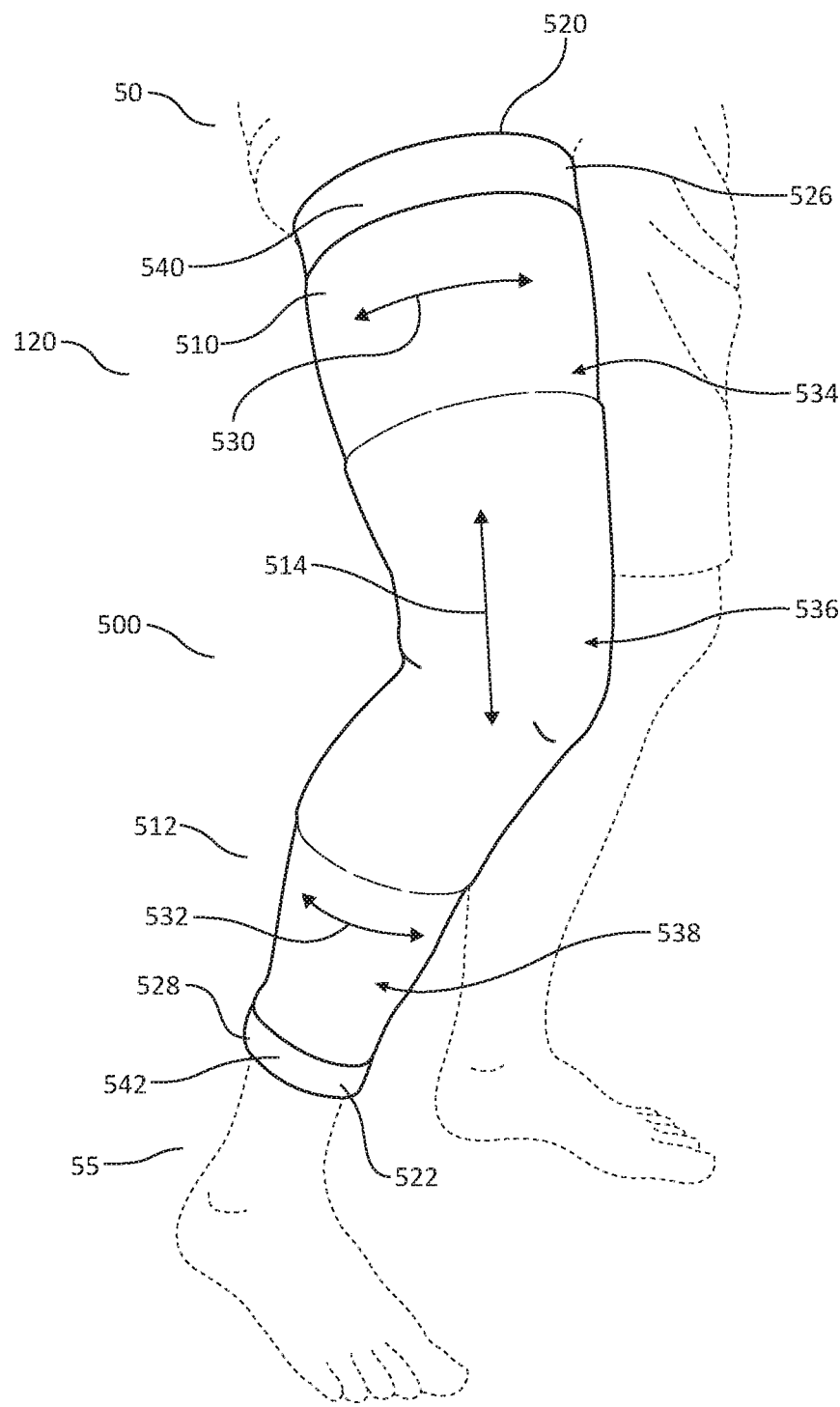
FIG. 20 is a perspective view of an embodiment of a sleeve assembly.

As shown in FIG. 20, in some embodiments, the sleeve assembly 120 may include a tubular member 500 having a first end 510, a second end 512, and a length in between 514. The tubular member first end 510 may define a first opening 520, and the tubular member second end 512 may define a second opening 522. The tubular member 500 may have a first inner diameter 530 at a section near the first end 510, and a second inner diameter 532 at a section near the second end 512. The first inner diameter 530 may be sized to receive the thigh 50 of a user when worn. The second inner diameter 532 may be sized to receive the shin 55 of a user when worn. In some embodiments, the various dimensions of the tubular member 500, such as the length 514, and the first and second inner diameter 530, 532 may be adjustable, or custom fitted to correspond to an anatomy of a user.

In some embodiments, the tubular member 500 may have a first outer surface 534, a second outer surface 536, and a third outer surface 538. The tubular member first end 510 may include a first cuff 540 surrounding the first opening 520. The tubular member second end 512 may include a second cuff 542 surrounding the second opening 522. The first and second cuffs 540, 542 may include additional feature such as a first closing device 526 and a second closing device 528. The first and second closing devices 526, 528 may include an elastic material, an elastic band, a belt, or any other means of adjusting the first and second openings 520, 522.

In some embodiments, the tubular member 500 may be formed from cloth, or textile that is relatively nonelastic. For example, the tubular member 500 may be formed from cloth or textile that is not elastic or stretchable. In some embodiments, the tubular member 500 may be formed from material that is elastic or stretchable. For example, the tubular member 500 may be formed from an elastic material that can compress or contract when placed on a leg of a user. In some embodiments, the first, second, and third outer surfaces 534, 536, 538 may include additional texture or surface material. For example, the first, second, or third outer surfaces 534, 536, 538 may include a non-slip material such as silicone, and/or include a non-slip pattern such as a raised surface.

The sleeve assembly 120 may be worn by a user by placing a foot or leg of a user into the tubular member first opening 520 and advancing the user's foot or leg along the length 514 of the tubular member 500. The user may advance the tubular member 500 along the leg until the foot and/or a portion of the user's leg is advance through the tubular member second opening 522.

Figure 21:
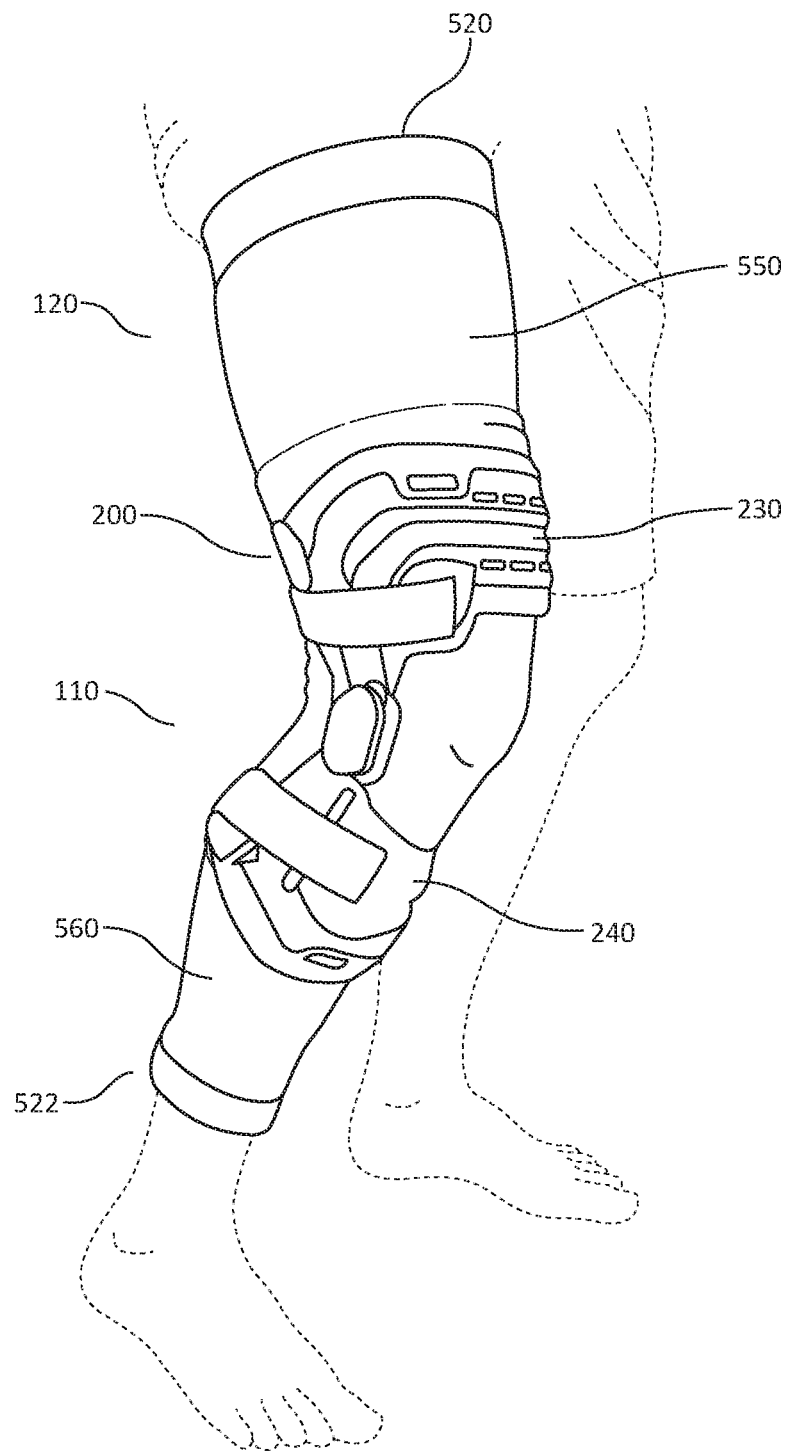
FIG. 21 is a perspective view of an embodiment of a knee brace assembly.

As shown in FIG. 21, the sleeve assembly 120 may be used with the frame assembly 200 to form a knee brace system 100. As shown in FIG. 21, the knee brace assembly 110 may be worn over the sleeve assembly 120 on the leg of a user. In some embodiments, the sleeve assembly 120 may be sized to fit the frame assembly 200. For example, the length or outer diameter of the sleeve assembly 120 may be sized to correspond to the length or inner diameter of the frame assembly 200. In some embodiments, the tubular member 500 may be longer than the frame assembly 200. For example, the tubular member 500 may have a first portion 550 that is not covered by the frame assembly top portion 230, and a second portion 560 that is not covered by the frame assembly bottom portion 240 when worn.

In some embodiments, the knee brace system 100 may be worn by first placing the sleeve assembly 120 on a user's leg, followed by placing the knee brace assembly 110 on the user's leg over the sleeve assembly 120. For example, as shown in FIG. 21, the sleeve assembly 120 may be worn by a user by placing a foot or leg of a user into the tubular member first opening 520 and advancing the user's foot or leg along the length 514 of the tubular member 500 until the foot and/or a portion of the user's leg is advanced through the tubular member second opening 522. After placing the sleeve assembly 120 on the user's leg, the knee brace assembly 110 may be placed on the user's leg by attaching the frame assembly 200 to the user's leg using a securement system such as the strap arrangement 210 previously described with reference to FIGS. 16 and 17.

Figure 22:
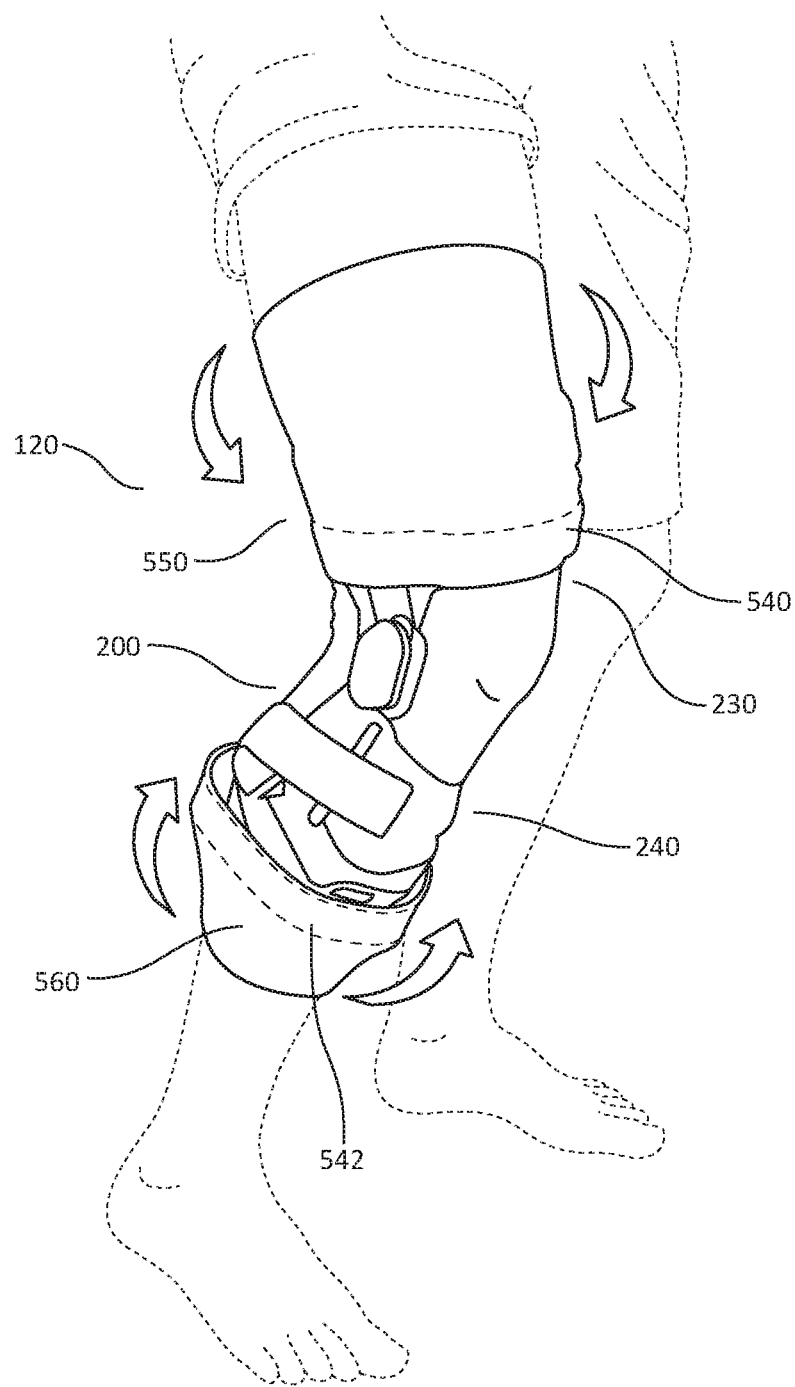
FIG. 22 is a perspective view of an embodiment of a knee brace assembly.

As shown in FIG. 22, after attaching the frame assembly 200 to the user's leg, the sleeve assembly 120 may be further manipulated to provide a more customized fit. In some embodiments, the sleeve assembly first portion 550 may be folded or rolled over the top portion 230 of the frame assembly 200 by inverting the tubular member first cuff 540 and advancing it over the outside of the knee brace assembly 110. The sleeve assembly second portion 560 may by folded or rolled over the bottom portion 240 of the frame assembly 200 by inverting the tubular member second cuff 542 and advancing it over the outside of the knee brace assembly 110. As shown in FIG. 22, this configuration allows the tubular member first outer surface (535 shown in FIG. 20) to fold over and contact the frame assembly first outer surface 220 (shown in FIG. 3). As shown in FIG. 22, the tubular member second outer surface (538 shown in FIG. 20) may be folded over and allowed to contact the frame assembly second outer surface 222 (shown in FIG. 3). In some embodiments, the tubular member first and second outer surface 535, 538 may include a non-slip or low slip surface, which may provide further securement to prevent the knee brace assembly 110 from moving relative to the user's leg when worn.

Figure 23:
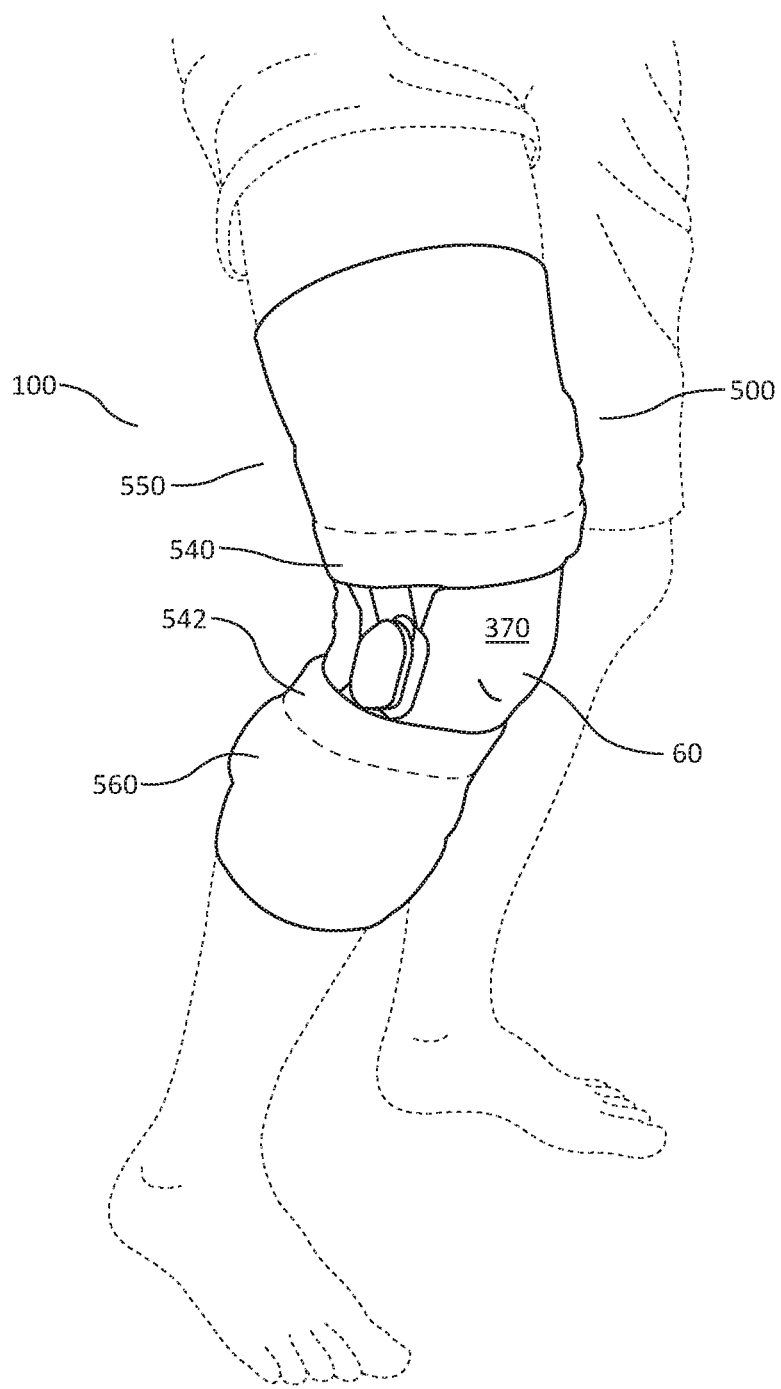
FIG. 23 is a perspective view of an embodiment of a knee brace assembly.

As shown in FIG. 23, in some embodiments, the knee brace system 100 may be in position on a user's leg with the sleeve assembly length 514 under the frame assembly 200, and a first and second portion 550, 560 over the top portion 230 and bottom portion 240 of the frame assembly 200. In some embodiments, the tubular member 500 may provide a further secured fit with the user's leg by positioning the first cuff 540 and second cuff 542 around the circumference of the user's leg and frame assembly 200 and inside the frame assembly central opening 370. For example, the tubular member first cuff 540 may be placed around the circumference of the user's leg and the frame assembly 200 and be positioned within the frame assembly central opening 370 adjacent the frame member top portion inner edge (275 shown in FIG. 3). Additionally or alternatively, the tubular member second cuff 542 may be placed around the circumference of the user's leg and the frame member 200 and be positioned within the frame assembly central opening 370 adjacent the frame member bottom portion inner edge (277 shown in FIG. 3). In this arrangement, the first cuff 540 provide a tight or snug fit between the user's knee 60 and the frame member top portion inner edge 275 in the front of the user's leg, and adjacent the bottom of a user's hamstring at the back of the user's leg. The second cuff 542 may also provide a tight or snug fit between the user's knee 60 and the frame member bottom portion inner edge 277 in the front of the user's leg, and adjacent the top of a user's calf at the back of the user's leg. This configuration may provide additional securement of the frame assembly 200 along the length of a user's leg when worn.

Figure 24:
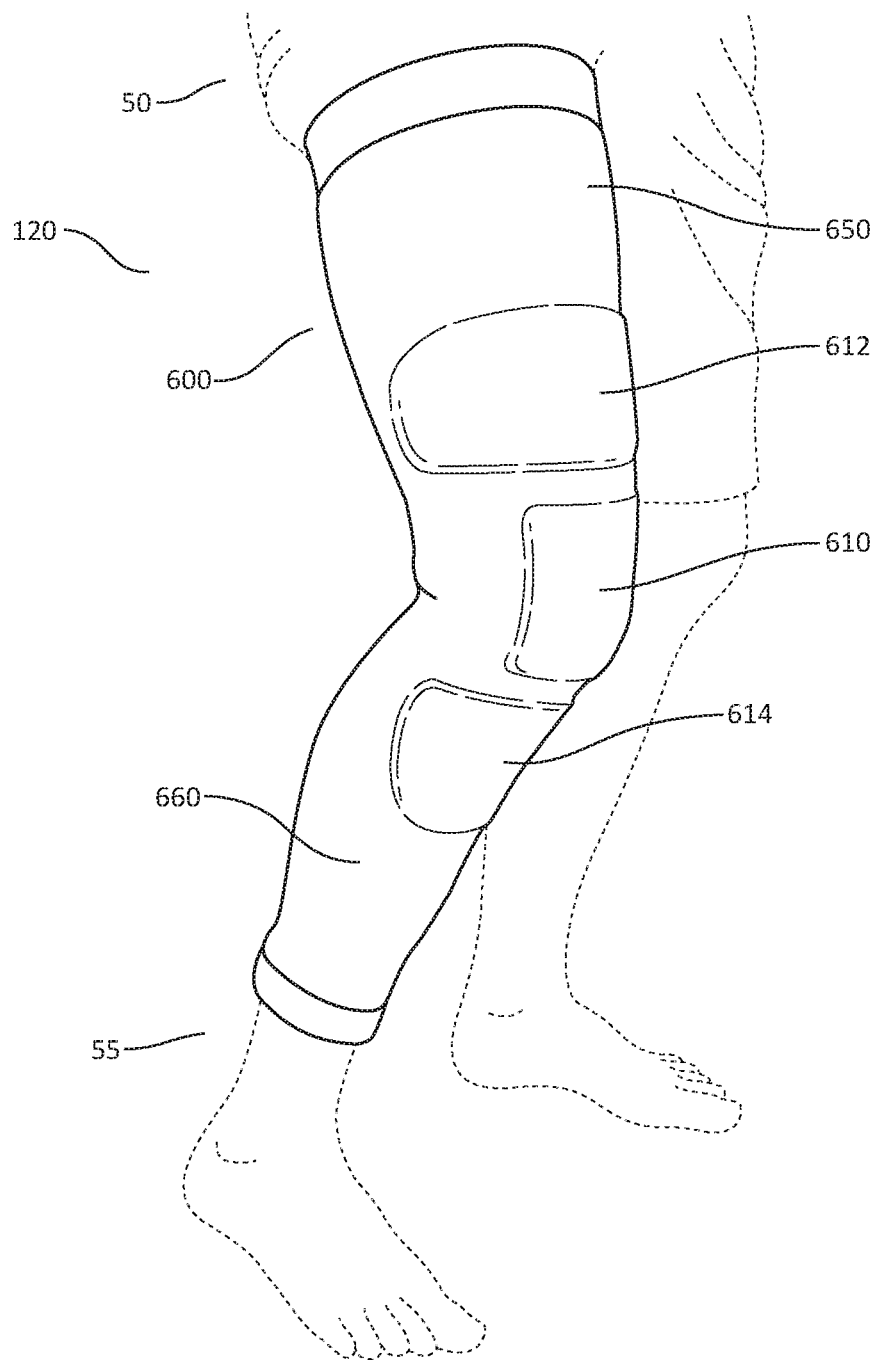
FIG. 24 is a perspective view of an embodiment of a knee brace assembly.

As shown in FIG. 24, in some embodiments, the sleeve assembly 120 may comprise a tubular member 600 having additional features. For example, as shown in FIG. 24, the tubular member 600 may have pads 610, 612, 614 attached or integrated with the tubular member 600. For example, a knee pad 610 may be configured to be located near a user's knee or patella when worn to cover part of a user's knee. In the embodiment shown in FIG. 24, the knee pad 610 may be configured to substantially cover a user's knee cap or patella when worn. In other embodiments, portions of the knee pad 610 may be removed in a region proximate a user's knee or patella. For example, the knee pad 610 may be configured as a circular or toroidal shape, with an opening to receive a user's patella when worn. In an additional embodiment, a circular knee pad 610 may form a patella buttress for supporting a user's patella when worn.

In some embodiments, the tubular member 600 may also include padding attached to the tubular member first portion 650 and/or second portion 660. In some embodiments a first pad 612 may be included with the tubular member first portion 650, and a second pad 614 may be included with the tubular member second portion 660. In some embodiments, the first pad 612 may be configured to cover or protect a user's upper leg, for example the thigh 50. In some embodiments, the second pad 614 may be configured to cover or protect parts of a user's lower leg on the front or the back. For example, the second pad 614 may be configured to be located adjacent to a user's calf or a shin 55 when worn.

Figure 25:
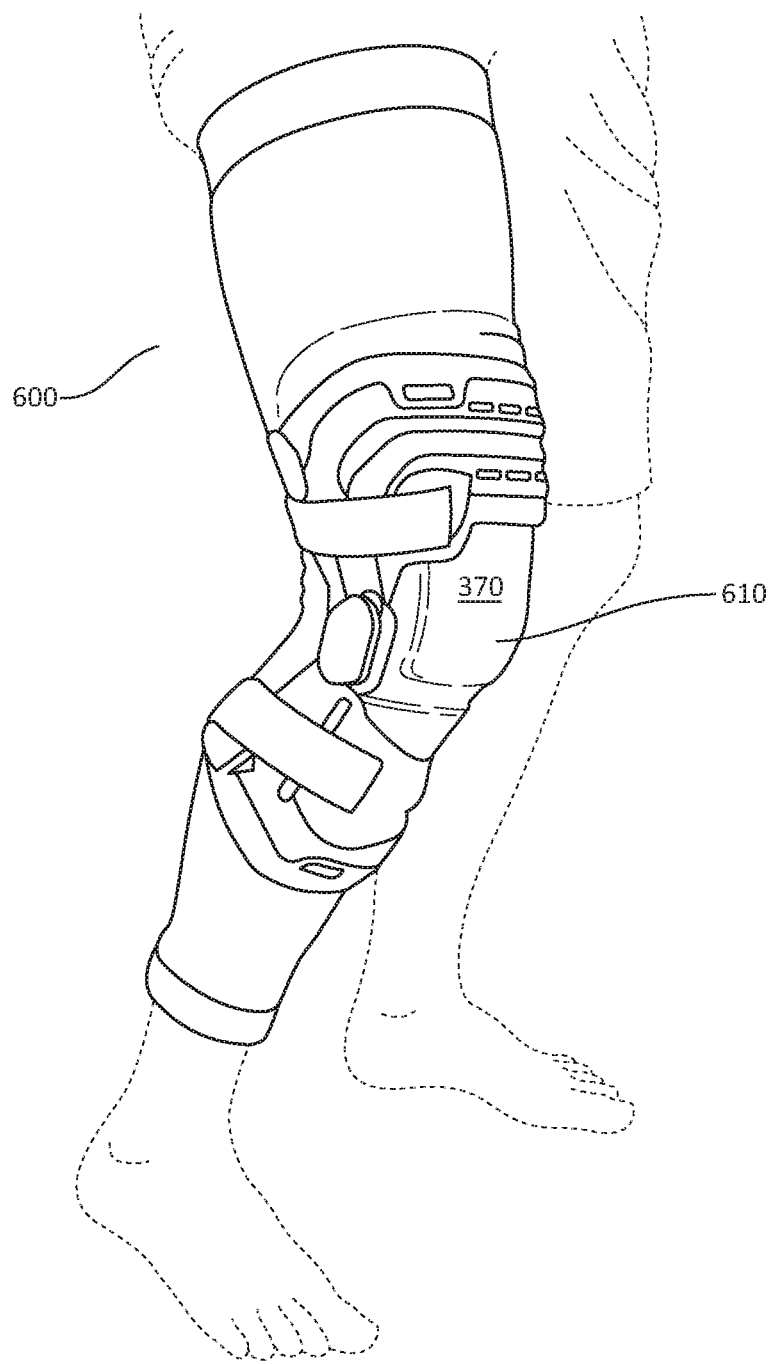
FIG. 25 is a perspective view of an embodiment of a knee brace assembly.

As shown in FIG. 25, the tubular member 600 may form part of a knee brace system 100 that provides an additional fit or protection to a user. For example, the sleeve assembly tubular member 600 that includes padding may be placed on the leg of a user with a similar procedure as described in reference to FIGS. 20 to 23. As shown in FIG. 25, the knee pad 610 may be located within the frame assembly central opening 370 and aligned to cover a user's knee 60. In some embodiments, the tubular member 600 may be placed on a user's leg with the pads 610, 612, 614 shown in FIG. 24, in a suitable position for interacting with a brace for a user's knee, such as the knee brace assembly 110 previously described. In some embodiments, the knee brace assembly 110 previously described in FIGS. 2 to 18, may be placed over a tubular member 600, with the top portion 230 located adjacent the first pad 612. Similarly, the knee brace assembly bottom portion 240 may be placed adjacent the tubular member second pad 614.

Figure 26:
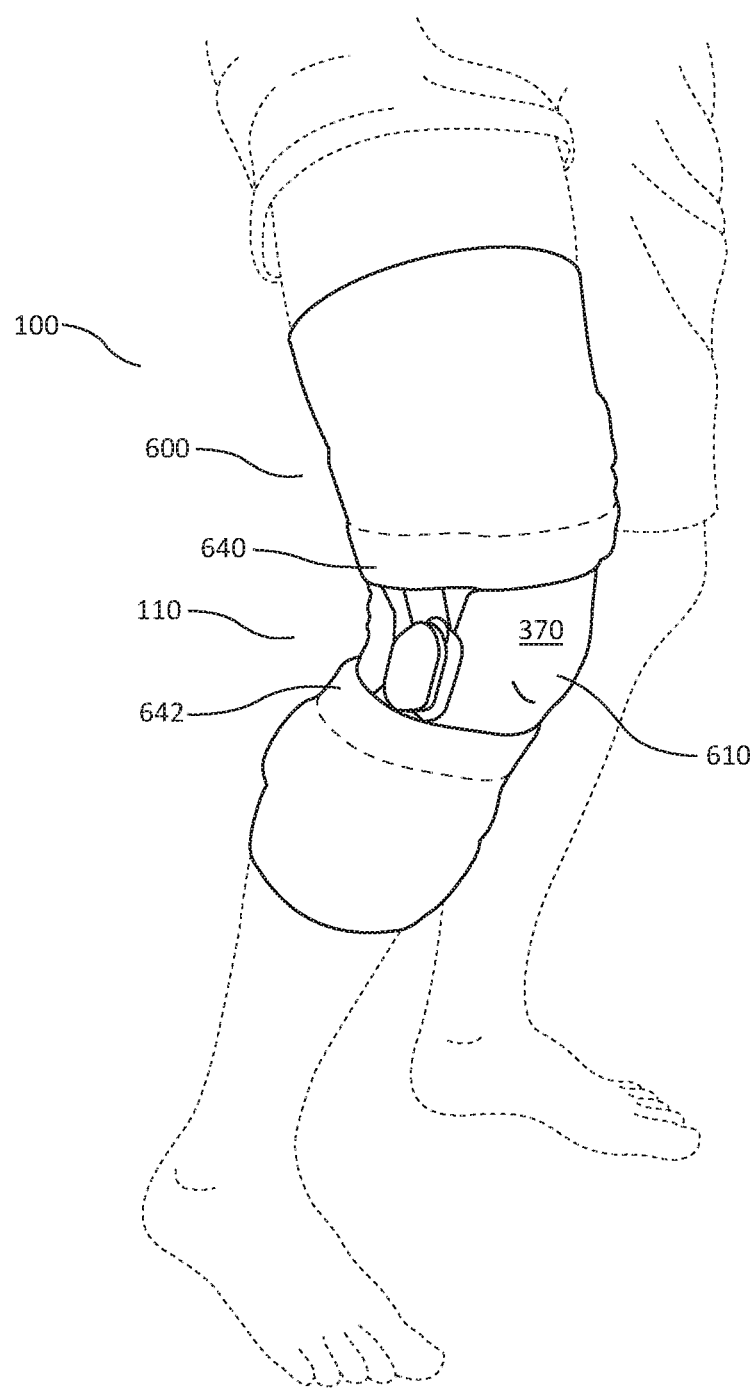
FIG. 26 is a perspective view of an embodiment of a knee brace assembly.

As shown in FIG. 26, after positioning the sleeve assembly tubular member 600 over the leg of a user, the knee pad 610 is positioned within the frame assembly central opening 370. As in the procedure described above with reference to FIG. 230, the tubular member 600 may include a first cuff 640 and second cuff 642 that are folded over the knee brace assembly 110 and form a fit with the user's leg to prevent movement of the knee brace system 100 relative to the user's knee when worn. In some embodiments, the tubular member 600 may be a suitable length to allow the first cuff 640 and the second cuff 642 to overlap when folded over the knee brace assembly 110. For example, the first cuff 540 may be folded over the knee brace assembly 110 and advanced past the central opening 370. Similarly, the second cuff may be folded over the knee brace assembly 110 and advanced past the central opening 370. Thus, in such an embodiment, after the first and second cuffs 640, 642 are in position, the knee brace assembly 110 may be substantially covered such that no parts of the knee brace assembly 110 are exposed. In some embodiments, the first and second cuffs 640, 642 may overlap after folding over the knee brace assembly 110. This may allow the sleeve assembly 120 to cover all external rigid parts of the knee brace assembly 110. Providing a system that allows all hard portions of a brace provides a desirable feature that addresses the regulations of sports that require no exposed hard parts on protective devices.

It is envisioned that the tubular members 500, 600 shown in FIGS. 20 to 26 may be used with knee braces or brace assemblies other than those described herein. That is, the sleeve assembly 120 may be used with knee braces or knee brace assemblies that are readily available in alternative configurations than those described herein.

Knee Brace System

As described herein, the knee brace assembly may be used with a sleeve assembly to form a knee brace system in combination. The knee brace assembly may include a molded high-impact support structure. The knee brace assembly may include rigid or semi-rigid lateral and medial support structures that are integrated to form an overall frame assembly. The knee brace assembly may include a first and second C-shaped support structures, and may include nested C-shaped support structures. The knee brace assembly may include a first lateral C-shape structure surrounding a smaller medial C-shaped structure, inverted in relation to the first lateral C-shape structure to create a lightweight, low profile, anatomically contoured, and/or articulating configuration, surrounding a user's knee or knee joint. The lateral and medial C-shaped structures may include hinges that provide a direct connection between the top and bottom portions and to fully integrate the brace & hinge assembly, while also allowing for targeted flex zones, for a semi-rigid fit.

In some embodiments, an over-molded flexible or resilient connection between the frame assembly members allows for an active self-adaptive flex-fit of the brace to be possible when a user's leg is flexing. Additionally, the thigh or calf musculature expansion & contraction and the compressive joint load produced by the weight of the body are accommodated by the flex-fit configuration. The over molded flex-fit zones connecting the C-shaped structures may also provide the ability for the overall sizing to adapt to the size of the user with a custom feeling fit within the targeted size range. This allows the brace to achieve a close, comfortable, correct fit for a broad range of users of various sizes.

An over-molded feature allows the brace to constantly interface with the user's body when in motion for the ideal fit while maintaining the integrity of the brace support performance with superior comfort. The over-molded material may also include the perimeter of the entire brace, providing a soft transition at the edges.

In some embodiments, the inner surface of the over molded semi-rigid structure is enhanced by comfortable foam lining pads in the thigh and shin contact areas of the brace that follow the anatomical contour of the brace and adjust with the self-adaptive flex fit of the brace. The pads may feature a multi-directional flexible design, with air-flow channels, moisture wicking, four-way stretch, and/or cover material, and are easily removed and reattached for washing.

In some embodiments, a securement system such as a strap assembly is used to attach the brace assembly to a user. The securement system is strategically positioned with pivot hardware anchored at the connections, with straps wrapping through the frame assembly providing direct tension transfer support within each of the top and bottom portions of the frame assembly. Multiple upper and upper and lower straps may allow for customization of adjustment for leg volume and preferred tension, for a precise, comfortable fit and anti-migration of the knee brace assembly during activity. In some embodiments, the straps may include comfortable, woven loop material, integrated with nylon webbing attached to pivot hardware and fixed to attachment positions. In some embodiments, the straps may be color coded to assist in directing a sequence of strapping for brace fitting. The strap assembly provides an easy-to-use, comfortable fit for extended periods of use and allows for replacement if a strap were to be lost or damaged.

In some embodiments, an anatomically patterned, four-way stretch, comfortable compression sleeve is integrated into the knee brace system. The sleeve may provide a moisture wicking anti-chaffing base layer between the skin and the brace assembly. With the brace and strap assembly in place on a user, the sleeve assembly ends may be wrapped over the upper and lower brace assembly, completely covering the frame assembly and strap assembly, providing an enhanced and evenly distributed compression fit. The sleeve assembly also inhibit strap ends being unintentionally loosened during activities and covers the over molded structure with a soft, close fitting cover. The sleeve assembly may have cuffs that may positioned adjacent to above and below the knee for a secure fit with that is comfortable throughout a user's range of motion. The combined features of the strap assembly and the sleeve assembly provide an superior stable and secure fit that keeps the knee brace system comfortably in place, even during the most intense activities.

In some embodiments, a range of optional sleeves may be selected from to be used with a knee brace assembly to accommodate specific needs for users requiring a higher level of impact protection, or patella support. For example, suitable features that may be integrated into sleeves include enhanced shin or thigh flex-fitting foam, a flex-fit knee pad, and/or a patella stability buttress. The sleeve assembly design also provide the potential for the sleeve assembly to have an increased extension from a bottom portion that extends beyond a user's shin and completely encases the hinges, covering all external hard parts of the brace. Providing a system that allows all hard portions of the brace provides a desirable feature that addresses the regulations of sports that require no exposed hard parts on protective devices.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. A knee brace system, comprising:
  a knee brace having a top portion and a bottom portion, the top portion including a top outer edge, and the bottom portion including a bottom outer edge; and
  a sleeve system including a tubular member having a first end defining a first opening, a first cuff adjacent the first opening and having a first elastic band, a second end defining a second opening, a second cuff adjacent the second opening and opposing the first cuff, and the second cuff having a second elastic band, a length in between the first and second ends, an inner surface, a first textured outer surface, and a second textured outer surface;
  wherein the tubular member is configured to receive a user's leg and the knee brace is configured to be positioned over a portion of the tubular member when worn, whereby the knee brace is securable to the user's leg, at least in part, by folding the first cuff over the top outer edge of the knee brace such that the first textured outer surface contacts the knee brace, and folding the second cuff over the bottom outer edge of the knee brace such that the second textured outer surface contacts the knee brace.

2. The knee brace system of claim 1, wherein the tubular member includes one or more pads configured to provide protection to the user's leg.

3. The knee brace system of claim 2, wherein the one or more pads includes a knee pad positioned to be located adjacent to a patella of the user's knee when worn.

4. The knee brace system of claim 2, wherein the one or more pads includes a first pad in-configured to cover the user's upper leg when worn.

5. The knee brace system of claim 1, wherein the knee brace comprises a frame assembly defining the top portion and the bottom portion of the knee brace, and wherein the top portion is pivotably connected to the bottom portion.

6. The knee brace system of claim 5, wherein the top portion of the frame assembly has an inner surface shaped to curve across a user's thigh, and wherein the bottom portion of the frame assembly has an inner surface shaped to curve across a user's shin, when worn by a user.

7. The knee brace system of claim 5, wherein the frame assembly includes a first articulation element configured to be located on a lateral side of a user's knee and a second articulation element configured to be located on a medial side of a user's knee when worn by a user.

8. The knee brace system of claim 5, further comprising a cushioning layer over molded around the top outer edge and bottom outer edge.

9. The knee brace system of claim 5, wherein the frame assembly has an opening configured to receive a knee of the user when worn.

10. The knee brace system of claim 9, wherein the tubular member further comprises a knee pad configured to be located adjacent a user's knee and at least partially within or adjacent to the opening in the frame assembly when worn.

* * * * *